United States Patent
Nakamura et al.

(10) Patent No.: US 11,129,523 B2
(45) Date of Patent: Sep. 28, 2021

(54) VISUAL FUNCTION EXAMINATION SYSTEM AND OPTICAL CHARACTERISTIC CALCULATION SYSTEM

(71) Applicants: VISUAL TECHNOLOGY LABORATORY INC., Tokyo (JP); MITSUI CHEMICALS, INC., Tokyo (JP)

(72) Inventors: Yoshiki Nakamura, Yokohama (JP); Sueko Kanaya, Ota-ku (JP); Noriaki Asada, Mobara (JP); Shoko Matsumura, Ichihara (JP); Akinori Nagatomo, Omuta (JP); Taizo Nishimoto, Chiba (JP)

(73) Assignees: VISUAL TECHNOLOGY LABORATORY INC., Tokyo (JP); MITSUI CHEMICALS, INC., Tokyo (JP)

( * ) Notice: Subject to any disclaimer, the term of this patent is extended or adjusted under 35 U.S.C. 154(b) by 259 days.

(21) Appl. No.: 16/311,369

(22) PCT Filed: Jul. 3, 2017

(86) PCT No.: PCT/JP2017/024334
§ 371 (c)(1),
(2) Date: Dec. 19, 2018

(87) PCT Pub. No.: WO2018/012334
PCT Pub. Date: Jan. 18, 2018

(65) Prior Publication Data
US 2019/0239741 A1    Aug. 8, 2019

(30) Foreign Application Priority Data
Jul. 11, 2016 (JP) .............................. JP2016-136992

(51) Int. Cl.
*A61B 3/00* (2006.01)
*A61B 3/06* (2006.01)
*A61B 3/024* (2006.01)

(52) U.S. Cl.
CPC .......... *A61B 3/0025* (2013.01); *A61B 3/0008* (2013.01); *A61B 3/0041* (2013.01);
(Continued)

(58) Field of Classification Search
CPC ..... A61B 3/0025; A61B 3/008; A61B 3/0041; A61B 3/0091; A61B 3/024; A61B 3/06; A61B 3/066
(Continued)

(56) References Cited

U.S. PATENT DOCUMENTS 7,654,673 B2 * 2/2010 Sung ...................... A61B 3/032
                                                                351/223
9,420,945 B2   8/2016 Coelho et al.
(Continued)

FOREIGN PATENT DOCUMENTS

JP          3963299 B2      8/2007
JP        2015-502238 A     1/2015

OTHER PUBLICATIONS

Aug. 9, 2019 Office Action issued in Russian Patent Application No. 2019100292.
Feb. 6, 2020 Extended European Search Report issued in European Patent Application No. 17827464.3.
Apr. 24, 2020 Office Action issued in Korean Patent Application No. 10-2018-7036546.
(Continued)

Primary Examiner — Zachary W Wilkes
(74) Attorney, Agent, or Firm — Oliff PLC

(57) ABSTRACT

An analysis unit determines at least two boundaries by determining; in a coordinate system indicating a correlation between a luminance contrast value between a luminance of an attention portion and a luminance of a background portion, and a luminance average value of a visual target including the attention portion and the background portion;
(Continued)

the boundary between a region where a subject has a visibility and a region where the subject does not have the visibility for each combination of stimulus values of a color stimulus of a visual target.

23 Claims, 27 Drawing Sheets

(52) U.S. Cl.
 CPC ............ *A61B 3/0091* (2013.01); *A61B 3/024* (2013.01); *A61B 3/06* (2013.01); *A61B 3/066* (2013.01); *A61B 2562/12* (2013.01)
(58) Field of Classification Search
 USPC ................................................ 351/237, 246
 See application file for complete search history.

(56) References Cited

U.S. PATENT DOCUMENTS

| | | | |
|---|---|---|---|
| 10,561,312 B2* | 2/2020 | Nordstrom | A61B 3/0008 |
| 10,674,903 B2* | 6/2020 | Tang | A61B 3/032 |
| 2010/0290006 A1 | 11/2010 | Flanagan et al. | |
| 2013/0155376 A1 | 6/2013 | Huang et al. | |

OTHER PUBLICATIONS

Fujikado et al. "Filters for Low Vision." Journal of the Eye, 2007, vol. 24, No. 9, pp. 1179-1186.
Sep. 19, 2017 International Search Report issued in International Patent Application No. PCT/JP2017/024334.

\* cited by examiner

A-0

B-0

C-0

D-0

A-N1

B-N1

C-N1

D-N1 a-01 b-01 c-01 d-01 a−02 b−02 c−02 d−02 a—N1 b—N1 c—N1 d—N1 a-C1 a-C2 a-C3 b-C1 b-C2 b-C3 c-C1 c-C2 c-C3 d-C1 d-C2 d-C3

ND OPTICAL CHARACTERISTIC
VISUAL FUNCTION EXAMINATION SYSTEM AND OPTICAL CHARACTERISTIC CALCULATION SYSTEM

CROSS REFERENCE TO RELATED APPLICATION

This application is a U.S. National Stage application claiming the benefit of prior filed International Application Number PCT/JP2017/024334, filed on Jul. 3, 2017, in which the International Application claims priority from Japanese Patent Application Number 2016-136992, filed on Jul. 11, 2016, the entire contents of which are incorporated herein by reference.

TECHNICAL FIELD

The present invention relates to a visual function examination system, an optical characteristic calculation system, a selection method of an optical member, a manufacturing method of an optical member, a manufacturing method of a display member, a manufacturing method of an illumination apparatus, a visual function examination device, an optical characteristic calculation device, a visual function examination method, a calculation method of an optical characteristic, a program, and a computer-readable storage medium.

BACKGROUND ART

An optical member such as a glass lens has optical characteristics such as a spectral transmittance and an X value, a Y value, and a Z value being tristimulus values of color. Regarding such optical characteristics, a means of calculating optical characteristics in accordance with a visual function of each individual based on a quantitative evaluation in an objective manner, and a means of selecting an optical member having the aforementioned optical characteristics, have not been developed yet. For example, in Non-Patent Document 1, a method of evaluating optical characteristics by utilizing conventional optometry apparatus and system is reported. In this method, a subject is required to try various optical members one by one.
Non-Patent Document 1: Fujikado et al., Journal of the Eye, 24(9), 1179-1186, 2007

DISCLOSURE

Problems to be Solved

When the optical characteristic is evaluated by utilizing the above-described conventional visual function examination, it is possible to select an optical member having an optical characteristic which is effective under a certain luminance condition when performing the visual function examination, but, there is a possibility that the effect cannot be obtained under a different luminance condition. Further, in the above-described method, a subject tries various optical members one by one and evaluates the optical characteristic subjectively.

The present invention has a proposition to establish a visual function examination which takes various luminance conditions including one at a time of examination into consideration, and a quantitative evaluation method in an objective manner regarding an optical characteristic of an optical member based on the visual function examination. In addition, the present invention has a proposition to establish a method in which there is no need to try various optical members when evaluating an optical characteristic.

Means for Solving the Problems

According to one aspect of embodiment of the present invention, a visual function examination system includes an analysis unit determining at least two boundaries by determining; in a coordinate system indicating a correlation between a luminance contrast value between a luminance of an attention portion and a luminance of a background portion, and a luminance average value of a visual target including the attention portion and the background portion; the boundary between a region where a subject has a visibility and a region where the subject does not have the visibility for each combination of stimulus values of a color stimulus of a visual target.

The visual function examination system may include a visual function examination unit sequentially presenting to the subject a visual target having at least one which is different in a combination of the luminance contrast value between the luminance of the attention portion and the luminance of the background portion, the luminance average value of the visual target including the attention portion and the background portion, and the stimulus values of the color stimulus of the visual target.

Further, the visual function examination unit may sequentially present to the subject a visual target having a same combination of the stimulus values of the color stimulus, and then sequentially present a visual target having a combination of the stimulus values of the color stimulus different from the visual target previously presented.

Further, the visual target may be displayed on a display device.

Further, the visual target may include a glare portion at a position within a visual field of the subject, and the glare portion may also displayed on the display device.

Further, in the coordinate system, a display unit displaying at least one boundary may be included.

According to another aspect of embodiment of the present invention, a visual function examination system includes an accepting unit accepting a result of a visual function examination obtained by sequentially presenting to a subject a visual target having at least one which is different in a combination of a luminance contrast value between a luminance of an attention portion and a luminance of a background portion, a luminance average value of a visual target including the attention portion and the background portion, and stimulus values of a color stimulus of a visual target; and based on the result of the visual function examination, an analysis unit determining, in a coordinate system indicating a correlation between the luminance contrast value and the luminance average value, the boundary between a region where the subject has a visibility and a region where the subject does not have the visibility for each combination of the stimulus values of the color stimulus.

According to one aspect of embodiment of the present invention, an optical characteristic calculation system includes a calculation unit calculating an optical characteristic of an optical member for compensating a visual function of the subject based on an examination result obtained by any one of the above-described visual function examination systems.

An accepting unit accepting the examination result obtained by the visual function examination system may be included.

Further, the calculation unit may calculate the optical characteristic of the optical member based on the examination result and a spectral distribution of a light source dominant in an environment where the subject uses the optical member.

Further, an acquiring unit acquiring information indicating a light source in an environment surrounding the subject as target information of a visibility of the subject, and a target value calculating unit calculating a target value in the coordinate system based on the target information may be included, in which the calculation unit may calculate the optical characteristic of the optical member based on the examination result and the target value.

According to one aspect of embodiment of the present invention, a selection method of an optical member selects an optical member based on the optical characteristic calculated by any one of the above-described optical characteristic calculation systems.

The optical characteristic may be received from the optical characteristic calculation system.

According to one aspect of embodiment of the present invention, a manufacturing method of an optical member manufactures an optical member based on the optical characteristic calculated by any one of the above-described optical characteristic calculation systems.

The optical characteristic may be received from the optical characteristic calculation system.

According to one aspect of embodiment of the present invention, a manufacturing method of a display member manufactures a display member based on the optical characteristic calculated by any one of the above-described optical characteristic calculation systems.

According to one aspect of embodiment of the present invention, a manufacturing method of an illumination apparatus manufactures an illumination apparatus based on the optical characteristic calculated by any one of the above-described optical characteristic calculation systems.

According to one aspect of embodiment of the present invention, a visual function examination device includes an analysis part determining at least two boundaries by determining; in a coordinate system indicating a correlation between a luminance contrast value between a luminance of an attention portion and a luminance of a background portion, and a luminance average value of a visual target including the attention portion and the background portion; the boundary between a region where a subject has a visibility and a region where the subject does not have the visibility for each combination of stimulus values of a color stimulus of a visual target.

A presentation part presenting the visual target to the subject, and an examination part executing a visual function examination which sequentially presents to the presentation part a visual target having at least one which is different in a combination of the luminance contrast value between the luminance of the attention portion and the luminance of the background portion, the luminance average value of the visual target including the attention portion and the background portion, and the stimulus values of the color stimulus of the visual target may be included.

According to one aspect of embodiment of the present invention, an optical characteristic calculation device includes a calculation part calculating an optical characteristic of an optical member for compensating a visual function of the subject based on an examination result obtained by any one of the above-described visual function examination devices.

According to one aspect of embodiment of the present invention, a visual function examination method determines at least two boundaries by determining; in a coordinate system indicating a correlation between a luminance contrast value between a luminance of an attention portion and a luminance of a background portion, and a luminance average value of a visual target including the attention portion and the background portion; the boundary between a region where a subject has a visibility and a region where the subject does not have the visibility for each combination of stimulus values of a color stimulus of a visual target.

Further, a visual target having at least one which is different in a combination of the luminance contrast value between the luminance of the attention portion and the luminance of the background portion, the luminance average value of the visual target including the attention portion and the background portion, and the stimulus values of the color stimulus of the visual target, may be sequentially presented to the subject.

According to one aspect of embodiment of the present invention, a calculation method of an optical characteristic calculates an optical characteristic of an optical member for compensating a visual function of the subject based on an examination result obtained by any one of the above-described visual function examination methods.

According to one aspect of embodiment of the present invention, a program causing a computer to execute processing of determining at least two boundaries by determining; in a coordinate system indicating a correlation between a luminance contrast value between a luminance of an attention portion and a luminance of a background portion, and a luminance average value of a visual target including the attention portion and the background portion; the boundary between a region where a subject has a visibility and a region where the subject does not have the visibility for each combination of stimulus values of a color stimulus of a visual target.

Further, a visual target having at least one which is different in a combination of the luminance contrast value between the luminance of the attention portion and the luminance of the background portion, the luminance average value of the visual target including the attention portion and the background portion, and the stimulus values of the color stimulus of the visual target, may be sequentially presented to the subject.

Further, an optical characteristic of an optical member may be calculated based on at least one of an examination result obtained by the processing of sequentially presenting the visual target to the subject, and an analysis result obtained by the processing of determining the boundaries.

According to one aspect of embodiment of the present invention, a computer-readable storage medium stores any one of the above-described programs.

According to the present invention, it is possible to realize a visual function examination which takes various luminance conditions including one when performing the examination into consideration.

DETAILED DESCRIPTION OF THE EMBODIMENTS

First Embodiment

Hereinafter, a visual function examination system of a first embodiment will be described by using the drawings.

Figure 1:
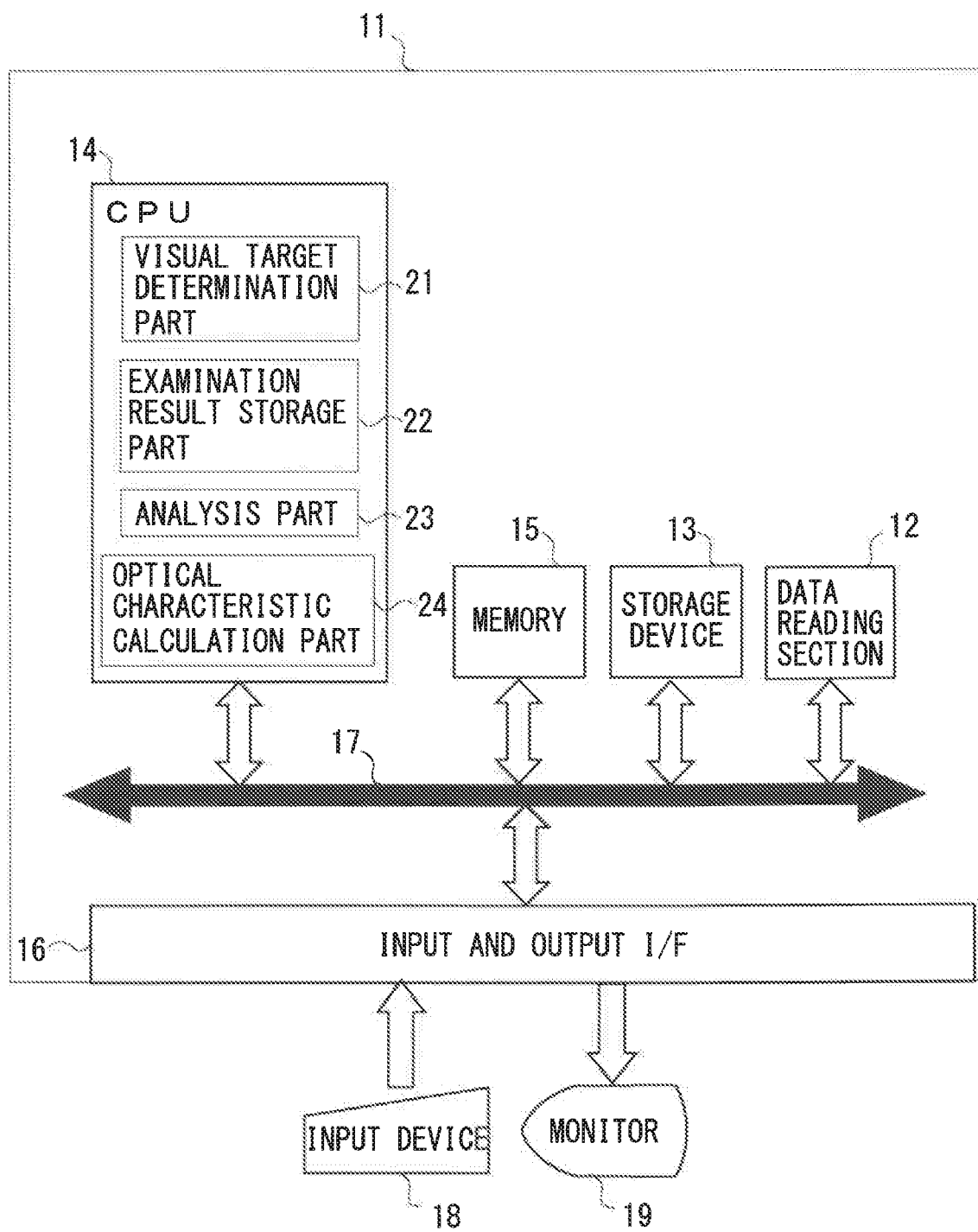
FIG. 1 is a block diagram illustrating a configuration of a visual function examination system of an embodiment.

As illustrated in FIG. 1, the visual function examination system of the first embodiment has a computer 11, an input device 18, and a monitor 19.

The computer 11 is a computer in which a visual function examination program of controlling respective parts of the visual function examination system is installed. As illustrated in FIG. 1, the computer 11 has a data reading section 12, a storage device 13, a CPU 14, a memory 15, an input and output I/F 16, and a bus 17. The data reading section 12, the storage device 13, the CPU 14, the memory 15, and the input and output I/F 16 are mutually connected via the bus 17. Besides, to the computer 11, the input device 18 (a keyboard, a pointing device, or the like), and the monitor 19 being one example of a display device are respectively connected via the input and output I/F 16. Note that the input and output I/F 16 accepts various Inputs from the input device 18, and outputs data for display to the monitor 19.

The data reading section 12 is used when the above-described visual function examination program is read from the outside. For example, the data reading section 12 is configured by a reading device (such as a reading device of an optical disk, a magnetic disk, or a magnetic optical disk) which acquires data from a detachable storage medium, or a communication device (such as a USB interface, a LAN module, or a wireless LAN module) which performs communication with an external device based on a publicly-known communication protocol.

The storage device 13 is configured by, for example, a storage medium such as a hard disk or a nonvolatile semiconductor memory. The storage device 13 stores the visual function examination program and various pieces of data which are necessary for executing the program.

The CPU 14 is a processor which comprehensively controls the respective parts of the computer 11. By the execution of the above-described visual function examination program, this CPU 14 functions as respective parts of a visual target determination part 21, an examination result storage part 22, an analysis part 23, and an optical characteristic calculation part 24. Details of the respective parts will be described later. Note that the respective parts of the visual target determination part 21, the examination result storage part 22, the analysis part 23, and the optical characteristic calculation part 24 may be configured in a manner of hardware by dedicated circuits.

The memory 15 temporarily stores various operation results obtained by the visual function examination program. This memory 15 is configured by, for example, a volatile SDRAM or the like.

The monitor 19 is, for example, a liquid crystal display device, an organic EL display device, or the like. It is possible to cite a case where the monitor 19 is installed at a height which is about a height of a line of sight (1.2 m from the ground, for example) when a subject is seated, with a distance of about 1 m, for example, from a position where the subject is seated.

Before explaining an operation of the visual function examination system with the configuration described above, an outline of the visual function examination will be first explained.

The visual function examination is an examination for acquiring information regarding an optical member which compensates a visual function of a subject. Here, the compensation of the visual function includes not only compensation for the purpose of improving a visibility, but also compensation which is accompanied by a reduction in the visibility, compensation of changing the visual function, compensation of optimizing the visual function, and so on. In the visual function examination, for example, a subject sees visual targets (details will be described later) which are sequentially displayed on the monitor 19, and a visibility of the subject regarding the visual target (for example, the subject can see/cannot see the visual target, the subject feels/does not feel the glare, and so on) is examined. The luminance condition at this time is, for example, a condition where, in the room, an outside light is cut off by a blackout curtain and an interior illumination is lit, by taking the easiness to see of the monitor 19 into consideration.

Note that the visual function examination includes a visibility examination which supposes a discomfort glare, and a visibility examination which supposes a disability glare. The discomfort glare indicates a case where a luminance difference between adjacent portions is significant, or a state where one feels uncomfortableness when an amount of light which is incident on an eye is rapidly increased. Further, the disability glare indicates a state where a contrast of a retinal image is lowered by a scattered light generated in an ocular tissue, which causes failure of eyesight. Details of the respective visibility examinations will be described later.

Figure 2:
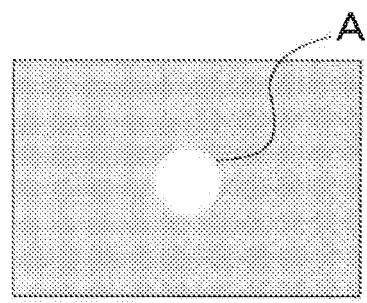
FIG. 2 is a diagram explaining a visual target of the embodiment.
Figure 3:
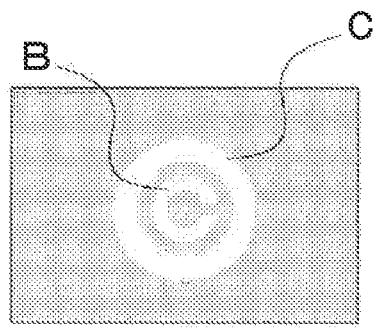
FIG. 3 is another diagram explaining the visual target of the embodiment.

Next, the visual targets will be described. In the present embodiment, two types of visual targets illustrated in FIG. 2 and FIG. 3 are used. The visual target illustrated in FIG. 2 has a circular portion A being an attention portion, and its background portion. This is used for the above-described visibility examination which supposes the discomfort glare. In the visibility examination using the visual target illustrated in FIG. 2, a subject sees the visual target from a position a certain distance away from the visual target, and judges the glare regarding the circular portion A. Note that in FIG. 2, one circular portion A is indicated, but, it is also possible that a plurality of circular portions A of two or more are displayed as the visual target on the monitor 19.

The visual target illustrated in FIG. 3 has a Landolt ring B being an attention portion and its background portion. A ring-shaped glare portion C is further provided, as a disturbance light, on the outside of the aforementioned visual target, and this is used for the above-described visibility examination which supposes the disability glare. The Landolt ring mentioned here is used for judging eyesight, and having a ring shape in which one portion in any direction is lacked, the direction being not limited to upper, lower, right, and left directions. In the visibility examination using the visual target illustrated in FIG. 3, a subject sees the visual target from a position a certain distance away from the visual target, and judges a direction of the lacked portion of the Landolt ring B. Note that in FIG. 3, one set of the Landolt ring B and the glare portion C is indicated, but, it is also possible that a plurality of the Landolt ring B and the glare portion C sets of two or more are displayed as the visual target on the monitor 19.

Note that the acquisition of the judgment result obtained by the subject may be performed by any method. For example, it is possible to configure such that the subject states the judgment result orally, an examiner performs hearing and then inputs the judgment result via the aforementioned input device 18 and input and output I/F 16, or it is possible to configure such that at least a part of the aforementioned input device 18 is prepared to the vicinity of the subject, and the subject inputs the judgment result via this input device 18 and the input and output I/F 16. Further, it is possible to configure such that a technique of voice recognition is utilized, and the Judgment result is input based on the voice of the subject.

In the present embodiment, the visual target is displayed on the aforementioned monitor 19. The visual target determination part 21 determines what kind of visual target is displayed on the monitor 19, and displays the determined visual target on the monitor 19 via the bus 17 and the input and output I/F 16. Regarding a brightness (luminance) of a screen of the monitor 19, if a maximum luminance is about 300 cd/m$^2$, for example, the display can also be performed at the luminance of 50% or less. Details regarding the contents of decision of the visual target determination part 21 will be described later.

The visual function examination system is for executing such a visual function examination and for obtaining, based on the result of the visual function examination, an optical characteristic of an optical member for compensating the visual function of the subject. The optical member is a piece that forms a part of a machine or an apparatus, and it is related to a phenomenon and a property of light (for example, an optical lens, an optical filter, and so on). In the present embodiment, explanation will be made on a visual function examination system in which an optical lens is targeted as one example of the optical member.

An operation of the visual function examination system described above will be described while referring to flow charts illustrated in FIG. 4 and FIG. 5.

In step S1, the CPU 14 controls the respective parts to perform the visual function examination. Details of the visual function examination will be described while referring to the flow chart (steps S11 to S18) illustrated in FIG. 5.

As described above, the visual function examination includes the visibility examination which supposes the discomfort glare, and the visibility examination which supposes the disability glare. In step S11 to step S13 illustrated in FIG. 5, the visibility examination which supposes the discomfort glare is performed by examining the brightness at which the subject feels the glare while changing the brightness of the circular attention portion of the visual target presented against a certain background. This examination can be performed in a necessary time of about three minutes, for example. Meanwhile, in step S14 to step S18 illustrated in FIG. 5, the visibility examination which supposes the disability glare is performed by examining a threshold value of the brightness at which the subject can visually recognize the direction of the lacked portion of the Landolt ring B while changing the brightness of at least one of the Landolt ring B being the attention portion of the visual target presented against a certain background and the ring-shaped glare portion disposed on the outside of the Landolt ring B. This examination can be performed in a necessary time of about ten minutes, for example.

In step S11, the CPU 14 performs a reference examination using the visual target including the circular attention portion. The reference examination is an examination to be a reference for an examination for acquiring information regarding an optical member which compensates the visual function of the subject. The reference examination in step S11 is an examination to be a control of an examination of an effect of an ND filter in step S12 and an examination of a color filter effect in step S13 to be described later.

Figure 6:
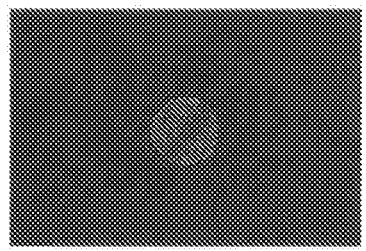
FIG. 6 is another diagram explaining the visual targets of the embodiment.
Figure 6:
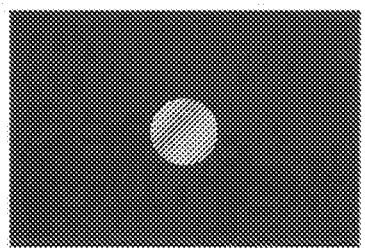
Figure 6:
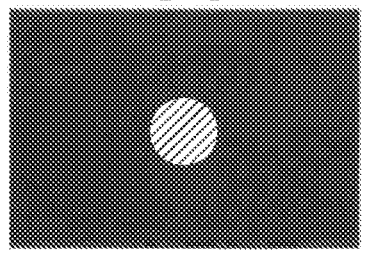
Figure 6:
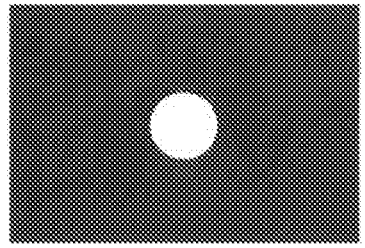

The CPU 14 makes the visual target determination part 21 sequentially display the visual targets each including the circular attention portion described in FIG. 2 on the monitor 19. In the present embodiment, as one example, the visual target determination part 21 displays the visual targets on the monitor 19 by sequentially changing the brightness of the circular attention portion from a dark state to a bright state in a certain presentation time. For example, the visual target determination part 21 sequentially changes the brightness of the circular attention portion presented against a certain background to brighter states in the order of A-0, B-0, C-0, and D-0, as illustrated in FIG. 6. The subject sees the visual target from a position a certain distance away from the visual target, and when the subject feels even the slightest glare, it is judged that "the glare is felt". This glare is caused by the discomfort glare, and indicates a state where the luminance difference between the certain background and the circular attention portion is significant in the visual function examination. When the reference examination is terminated, the CPU 14 stores the visual target in which the brightness of the circular attention portion is darker by one stage than that of the visual target regarding which it is Judged that "the glare is felt", in the examination result storage part 22 as an examination result, and the process proceeds to step S12.

Note that it is also possible that the visual target determination part 21 simultaneously displays the four attention portions with different brightness of A-0, B-0, C-0, and D-0 on the monitor 19, and the subject makes a judgment by comparing the four attention portions, for example.

In step S12, the CPU 14 performs the examination of the ND filter effect. The examination of the ND filter effect is an examination performed in a state of reducing only a light amount. In the examination of the ND filter effect, by comparing a result thereof with the reference examination in step S11 described above, it is possible to acquire information regarding an influence of the light amount with respect to the visual function of the subject. As one example of the ND filter effect, there is a light-shielding effect brought by so-called sunglasses. The sunglasses mentioned here indicate eyeglasses having lenses which cut, not a specific wavelength, but all wavelengths in an average manner, in order to reduce the glare.

Figure 7:
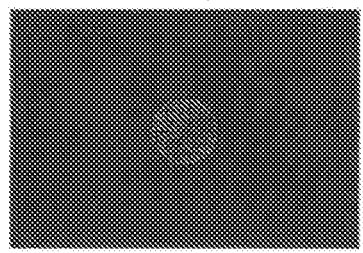
FIG. 7 is another diagram explaining the visual targets of the embodiment.
Figure 7:
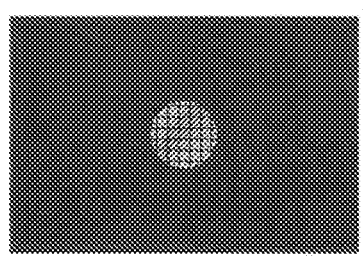
Figure 7:
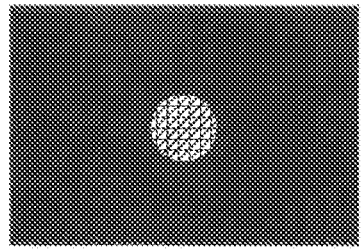
Figure 7:
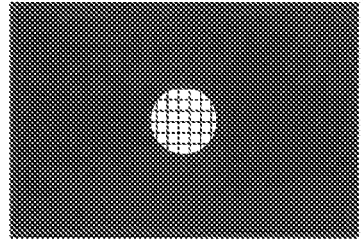

The CPU 14 makes the visual target determination part 21 sequentially display, on the monitor 19, visual targets whose brightness is set to 50%, for example, with respect to the brightness of the visual targets each including the circular attention portion and used in the reference examination described in step S11. Concretely, A-N1, B-N1, C-N1, and D-N1, as illustrated in FIG. 7, whose brightness is set to 50% of the brightness of the respective visual targets (A-0, B-0, C-0, and D-0) described by using FIG. 6, are sequentially presented to the monitor 19 by the visual target determination part 21. The subject makes a judgment similarly to step S11. When the examination of the ND filter effect is terminated, the CPU 14 stores the visual target in which the brightness of the circular attention portion is darker by one stage than that of the visual target regarding which it is judged that "the glare is felt", in the examination result storage part 22 as an examination result, and the process proceeds to step S13.

Note that it is also possible that the visual target determination part 21 simultaneously displays the four attention portions with different brightness of A-N1, B-N1, C-N1, and D-N1 on the monitor 19, and the subject makes a judgment by comparing the four attention portions, for example. Besides, the visual target determination part 21 may also display the judgment results obtained by the subject by a list on the monitor 19.

In step S13, the CPU 14 performs the examination of the color filter effect. The examination of the color filter effect is an examination performed by changing a spectral characteristic of the monitor 19. In the examination of the color filter effect, by comparing a result thereof with the reference examination in step S11 described above, it is possible to acquire information regarding a first influence indicating an influence of a light amount with respect to the visual function of the subject, and a second influence indicating an influence of a combination of stimulus values of a color stimulus. As one example of the color filter effect, there is an effect brought by eyeglasses having so-called color lenses. The color lenses mentioned here indicate optical lenses for eyeglasses having lenses with a spectral transmittance in which a specific wavelength is cut.

Figure 8:
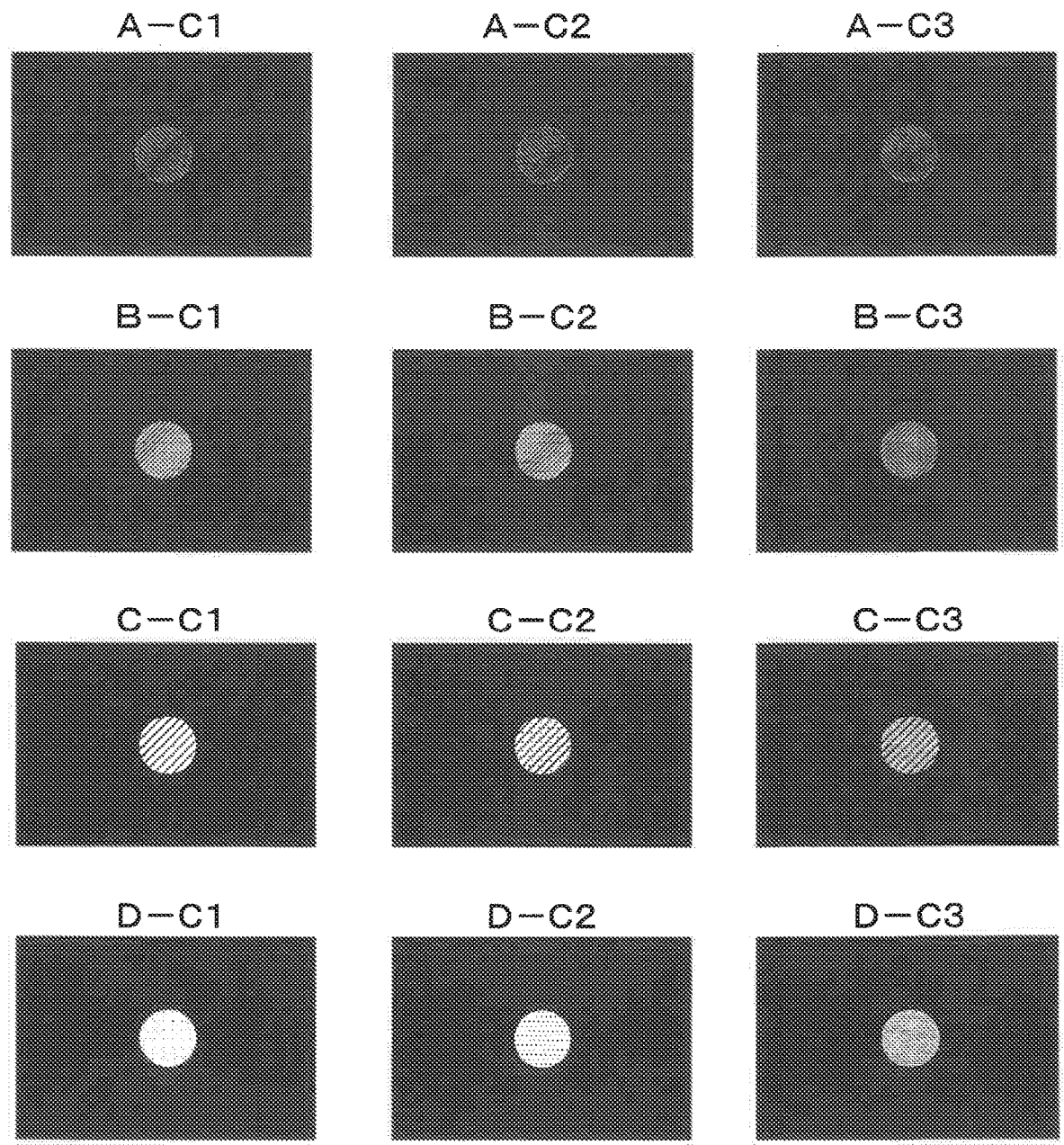
FIG. 8 is another diagram explaining the visual targets of the embodiment.

The CPU 14 makes the visual target determination part 21 sequentially display, on the monitor 19, visual targets having a combination of stimulus values of a color stimulus different from that of the visual targets each including the circular attention portion and used in the reference examination described in step S11. For example, the visual target determination part 21 sequentially presents, to the monitor 19, A-C1, B-C1, C-C1, and D-C1, as illustrated in FIG. 8, whose color stimulus value of R is set to 50% of the color stimulus value of R of the respective visual targets (A-0, B-0, C-0, and D-0) described by using FIG. 6. Further, the visual target determination part 21 sequentially presents A-C2, B-C2, C-C2, and D-C2 whose color stimulus value of G is set to 50%, and then it sequentially presents, to the monitor 19, A-C3, B-C3, C-C3, and D-C3 whose color stimulus value of B is set to 50%, as illustrated in FIG. 8. Note that when the stimulus value of R is set to 50%, each visual target has a blue color, when the stimulus value of G is set to 50%, each visual target has a red color, and when the stimulus value of B is set to 50%, each visual target has a yellow color. The subject makes a judgment similarly to step S11 and step S12. When the examination of the color filter effect is terminated, the CPU 14 stores respective visual targets in each of which the brightness of the circular attention portion is darker by one stage than that of the visual target regarding which it is judged that "the glare is felt", in the examination result storage part 22 as examination results, and the process proceeds to step S14. Note that in step S13, the examination is performed by using three patterns of visual targets with different combinations of the stimulus values of the color stimulus, so that there are three types of examination results. Further, the three types of examination results differ due to the visual function of the subject.

Note that it is also possible that the visual target determination part 21 simultaneously displays a plurality of attention portions with mutually different colors on the monitor 19 and changes the brightness of each of the attention portions, and the subject makes a judgment of the brightness of each color, for example. Further, a portion where the attention portion is not presented, may also be presented in a color of gray.

In step S14, the CPU 14 performs a size examination of the Landolt ring B. This examination is for selecting a size of the Landolt ring B by which the subject can easily recognize a direction of a lacked portion in the visual function examination to be performed thereafter.

Figure 9:
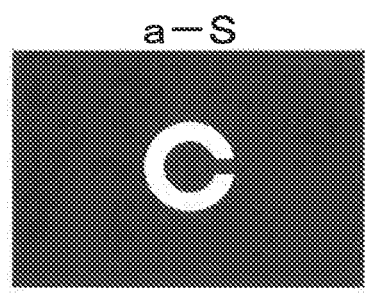
FIG. 9 is another diagram explaining the visual targets of the embodiment.
Figure 9:
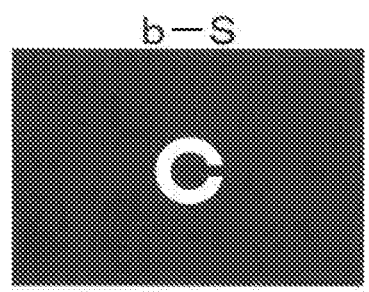
Figure 9:
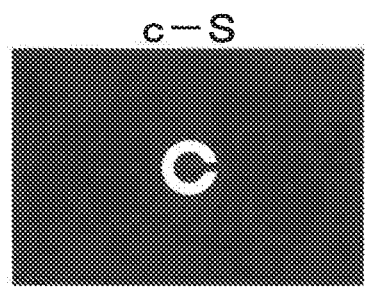
Figure 9:
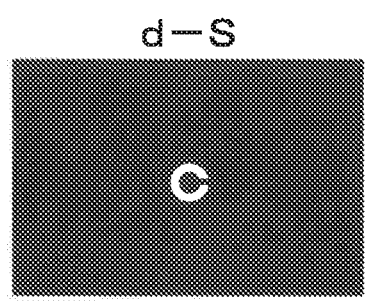

The CPU 14 makes the visual target determination part 21 sequentially display visual targets each having the Landolt ring B on the monitor 19. In the present embodiment, as one example, the visual target determination part 21 displays the visual targets on the monitor 19 by sequentially changing the size of the Landolt ring B. For example, the visual target determination part 21 sequentially changes the size of the Landolt ring B presented against a certain background in the order of a-S, b-S, c-S, and d-S, as illustrated in FIG. 9. The subject sees the visual target from a position a certain distance away from the visual target, and judges the size of the Landolt ring B by which the subject can easily recognize a direction of the lacked portion. When the size examination of the Landolt ring B is terminated, the CPU 14 stores the result with the use of the examination result storage part 22, and the process proceeds to step S15.

In step S15, the CPU 14 performs a reference examination using the Landolt ring B. This reference examination is an examination to be a reference for an examination for acquiring information regarding an optical member which compensates the visual function of the subject. The reference examination in step S15 is an examination to be a control of an examination of an effect of an ND filter in step S17 and an examination of a color filter effect in step S18 to be described later.

Figure 10:
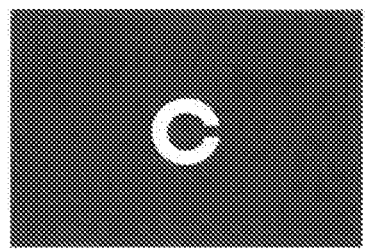
FIG. 10 is another diagram explaining the visual targets of the embodiment.
Figure 10:
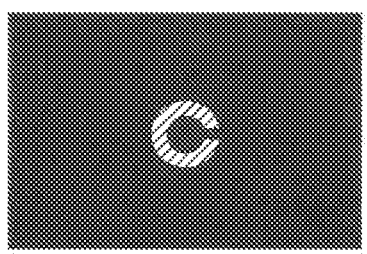
Figure 10:
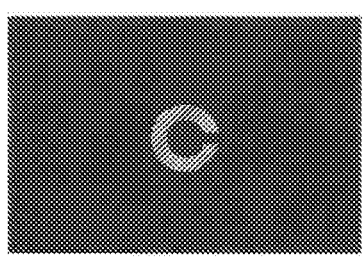
Figure 10:
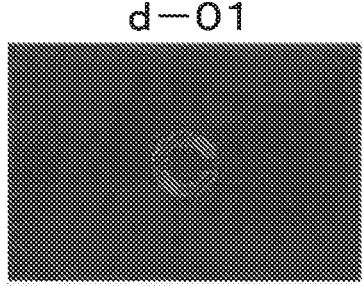

The CPU 14 makes the visual target determination part 21 sequentially display the Landolt ring B whose size is determined in step S14, on the monitor 19. In the present embodiment, as one example, the visual target determination part 21 displays the Landolt ring B on the monitor 19 by sequentially changing the brightness of the Landolt ring B from a bright state to a dark state. For example, the visual target determination part 21 sequentially changes the brightness of the Landolt ring B presented against a certain background to darker states in the order of a-01, b-01, c-01, and d-01, as illustrated in FIG. 10. The subject sees the visual target from a position a certain distance away from the visual target to judge the visibility. When the reference examination is terminated, the CPU 14 stores the visual target in which the brightness of the Landolt ring B is brighter by one stage than that of the visual target judged as "incapable of being visually recognized", in the examination result storage part 22 as an examination result, and the process proceeds to step S16.

Note that the CPU 14 may also change a contrast by using a simple up-and-down method and a transformed up-and-down method at the vicinity of a threshold value indicating a boundary between the brightness of the Landolt ring B judged as "incapable of being visually recognized" and the brightness of the Landolt ring B judged as "capable of being visually recognized", for example. Further, it is also possible that the CPU 14 calculates an average value of stimulus values of inverted point, and decides a luminance contrast value and a luminance average value by using the calculated average value.

In step S16, the CPU 14 performs a reference examination by adding a ring-shaped glare portion to the outside of the Landolt ring B. This reference examination is an examination to be a reference for an examination for acquiring information regarding an optical member which compensates the visual function of the subject. The reference examination in step S16 is an examination to be a control of the examination of the effect of the ND filter in step S17 and the examination of the color filter effect in step S18 to be described later, similarly to the examination in step S15 described above.

Figure 11:
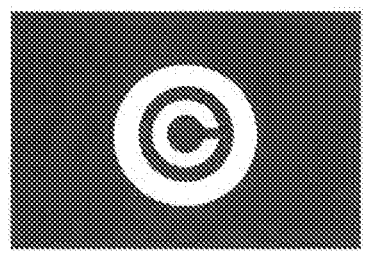
FIG. 11 is another diagram explaining the visual targets of the embodiment.
Figure 11:
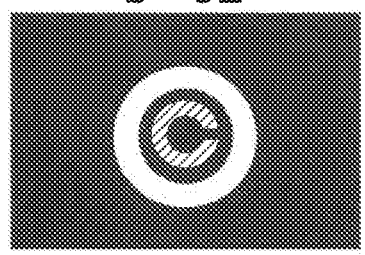
Figure 11:
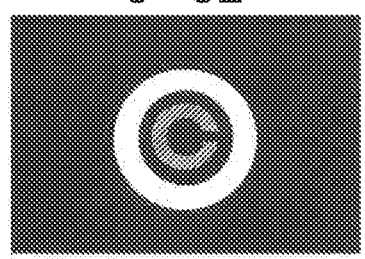
Figure 11:
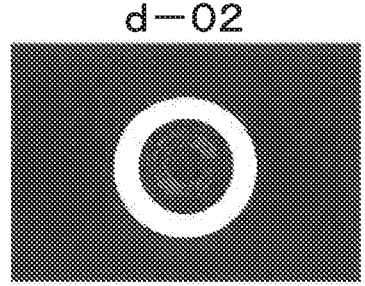

The CPU 14 makes the visual target determination part 21 sequentially display, on the monitor 19, the visual target including the Landolt ring B and the ring-shaped glare portion disposed on the outside of the Landolt ring B described in FIG. 3. At this time, the visual target determination part 21 sets the brightness of the glare portion to be constant, but, it sequentially changes the brightness of the Landolt ring B from the bright state to the dark state. In the present embodiment, the visual target determination part 21 sequentially changes the brightness of the Landolt ring B to darker states in the order of a-02, b-02, c-02, and d-02, with respect to the glare portion having a certain brightness and presented against a certain background, as illustrated in FIG. 11, for example. The subject sees the visual target from a position a certain distance away from the visual target and judges the visibility. Generally, the visibility deteriorates when the glare portion is added. This reduction in the visibility is caused by the disability glare. The disability glare indicates a state where a contrast of a retinal image is lowered by a scattered light generated in an eye, which causes reduction in the visual function. When the reference examination is terminated, the CPU 14 stores the visual target in which the brightness of the Landolt ring B is brighter by one stage than that of the visual target Judged as "incapable of being visually recognized", in the examination result storage part 22 as an examination result, and the process proceeds to step S17.

In step S17, the CPU 14 performs the examination of the ND filter effect similarly to step S12 described above.

Figure 12:
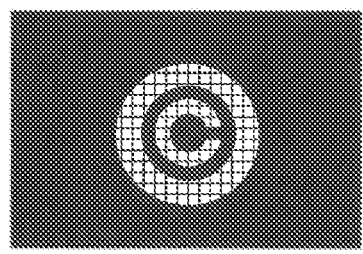
FIG. 12 is another diagram explaining the visual targets of the embodiment.
Figure 12:
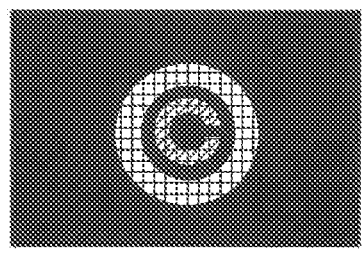
Figure 12:
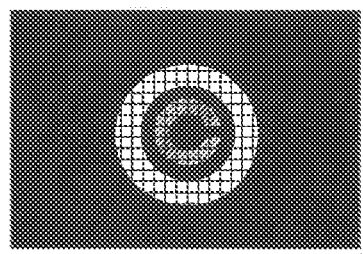
Figure 12:
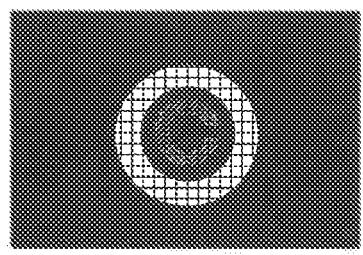

The CPU 14 makes the visual target determination part 21 sequentially display, on the monitor 19, the visual target including the Landolt ring B and the ring-shaped glare portion disposed on the outside of the Landolt ring B used in the reference examination described in step S16 whose brightness is set to 50%, for example. Concretely, as illustrated in FIG. 12, the visual target determination part 21 sequentially displays a-N1, b-N1, c-N1, and d-N1 whose brightness is set to 50% of the brightness of the respective visual targets (a-02, b-02, c-02, and d-02) described by using FIG. 11. The subject makes a judgment similarly to step S15 and step S16. When the examination of the ND filter effect is terminated, the CPU 14 stores the visual target in which the brightness of the Landolt ring B is brighter by one stage than that of the visual target judged as "incapable of being visually recognized", in the examination result storage part 22 as an examination result, and the process proceeds to step S18.

In step S18, the CPU 14 performs the examination of the color filter effect similarly to step S13 described above.

Figure 13:
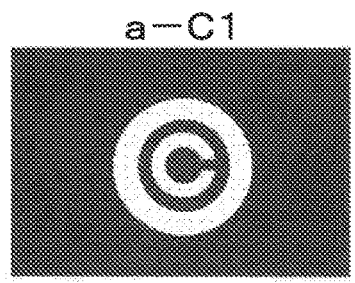
FIG. 13 is another diagram explaining the visual targets of the embodiment.
Figure 13:
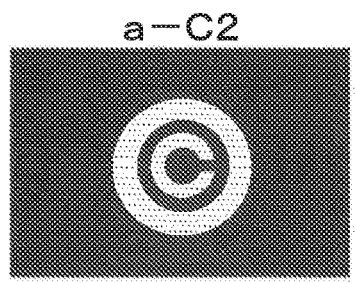
Figure 13:
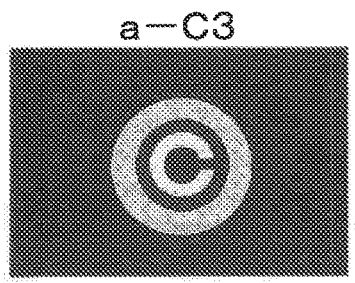
Figure 13:
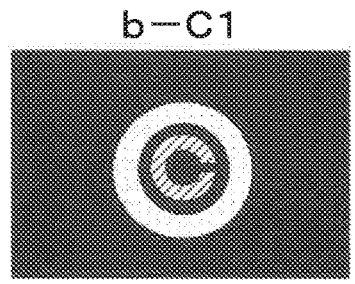
Figure 13:
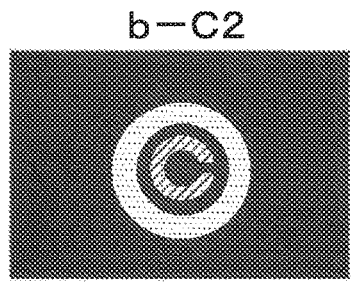
Figure 13:
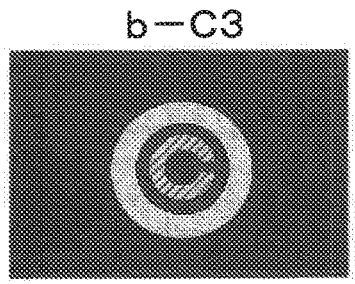
Figure 13:
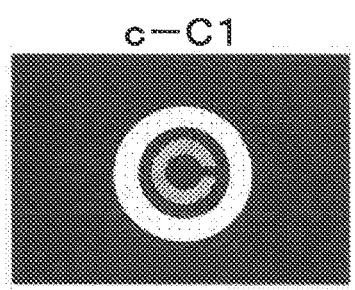
Figure 13:
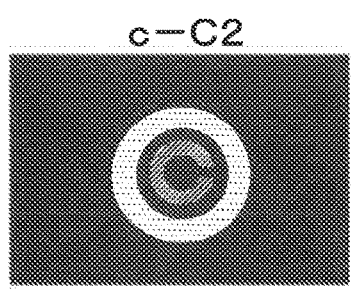
Figure 13:
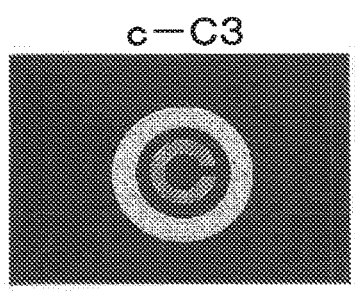
Figure 13:
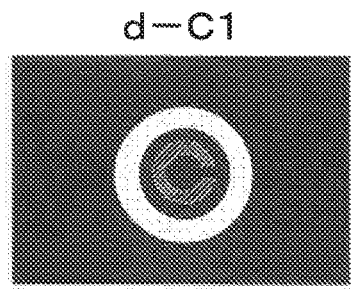
Figure 13:
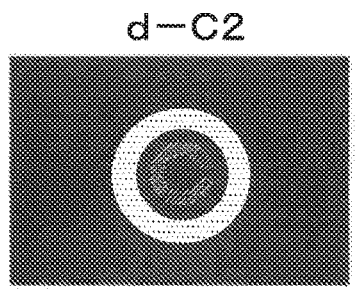
Figure 13:
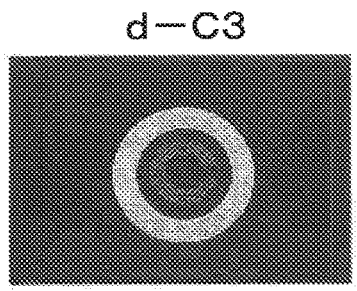

The CPU 14 makes the visual target determination part 21 sequentially display, on the monitor 19, the visual target including the Landolt ring B and the ring-shaped glare portion disposed on the outside of the Landolt ring B used in the reference examination described in step S16 with different combination of stimulus values of the color stimulus. For example, as illustrated in FIG. 13, the visual target determination part 21 sequentially presents a-C1, b-C1, c-C1, and d-C1 whose color stimulus value of R is set to 50% of the color stimulus value of R of the respective visual targets (a-02, b-02, c-02, and d-02) described by using FIG. 11. Further, as Illustrated in FIG. 13, the visual target determination part 21 sequentially presents a-C2, b-C2, c-C2, and d-C2 whose color stimulus value of G is set to 50%, and then sequentially presents a-C3, b-C3, c-C3, and d-C3 whose color stimulus value of B is set to 50%. The subject makes a judgment similarly to step S15 to step S17. When the examination of the color filter effect is terminated, the CPU 14 stores the visual targets in each of which the brightness of the Landolt ring B is brighter by one stage than that of the visual target Judged as "incapable of being visually recognized", in the examination result storage part 22 as examination results and terminates the visual function examination, and the process proceeds to step S2 illustrated in FIG. 4.

Note that the visual function examination described so far is one example, and it is not limited to this example. For example, it is also possible to configure such that only either the visibility examination which supposes the discomfort glare or the visibility examination which supposes the disability glare is performed, or the examinations are performed by switching the order thereof. Further, although the example in which both of the examination of the ND filter effect and the examination of the color filter effect are performed in both of the visibility examination which supposes the discomfort glare and the visibility examination which supposes the disability glare is described, it is also possible to configure such that only either the examination of the ND filter effect or the examination of the color filter effect is performed. Further, for example, in the visibility examination which supposes the disability glare, the visual target including the Landolt ring B and the ring-shaped glare portion disposed on the outside of the Landolt ring B are exemplified, but, the glare portion may also have a shape other than the ring shape.

Figure 4:
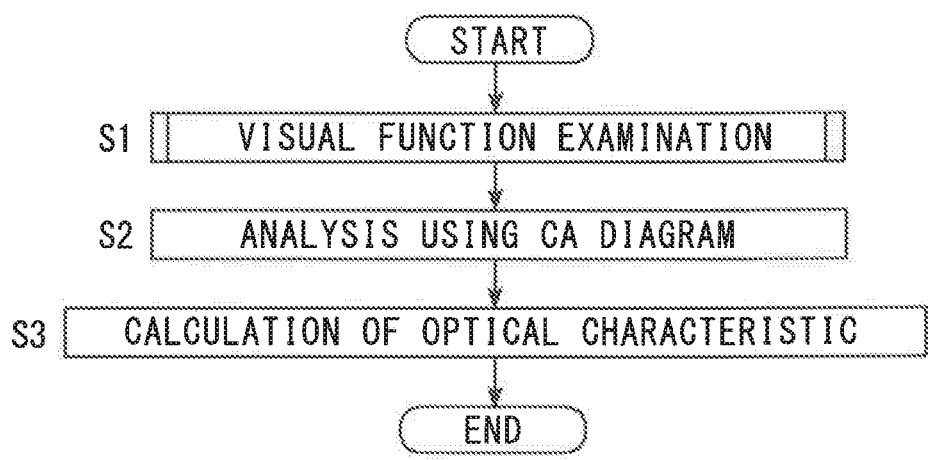
FIG. 4 is a flow chart indicating an operation of the visual function examination system of the embodiment.

In step S2 illustrated in FIG. 4, the CPU 14 makes the analysis part 23 perform an analysis by using a CA diagram. The CA diagram is a two-dimensional evaluation diagram of the visibility in which a vertical axis takes a luminance contrast value (Contrast) and a horizontal axis takes a luminance average value (Average Luminance), and is a coordinate system indicating a correlation between the luminance contrast value and the luminance average value. The CA diagram is disclosed in detail by the inventors in Japanese Patent No. 3963299.

The luminance contrast value is a value indicating a contrast between a luminance of an attention portion of a visual target and a luminance of a background portion of the visual target. In the visual target illustrated in FIG. 2, a value indicating a contrast between a luminance of the circular portion being the attention portion and a luminance of the background portion corresponds to the luminance contrast value. Meanwhile, in the visual target illustrated in FIG. 3, the Landolt ring B is the attention portion, and the outside of the Landolt ring B and an inside of the ring-shaped glare portion correspond to the background portion, as described above. Further, the luminance average value is a value indicating a luminance average value of the visual target including the attention portion and the background portion. In the present embodiment, a logarithmic luminance average value is used as one example of the luminance average value. Note that the luminance contrast value and the luminance average value may be calculated by any calculation method.

Figure 5:
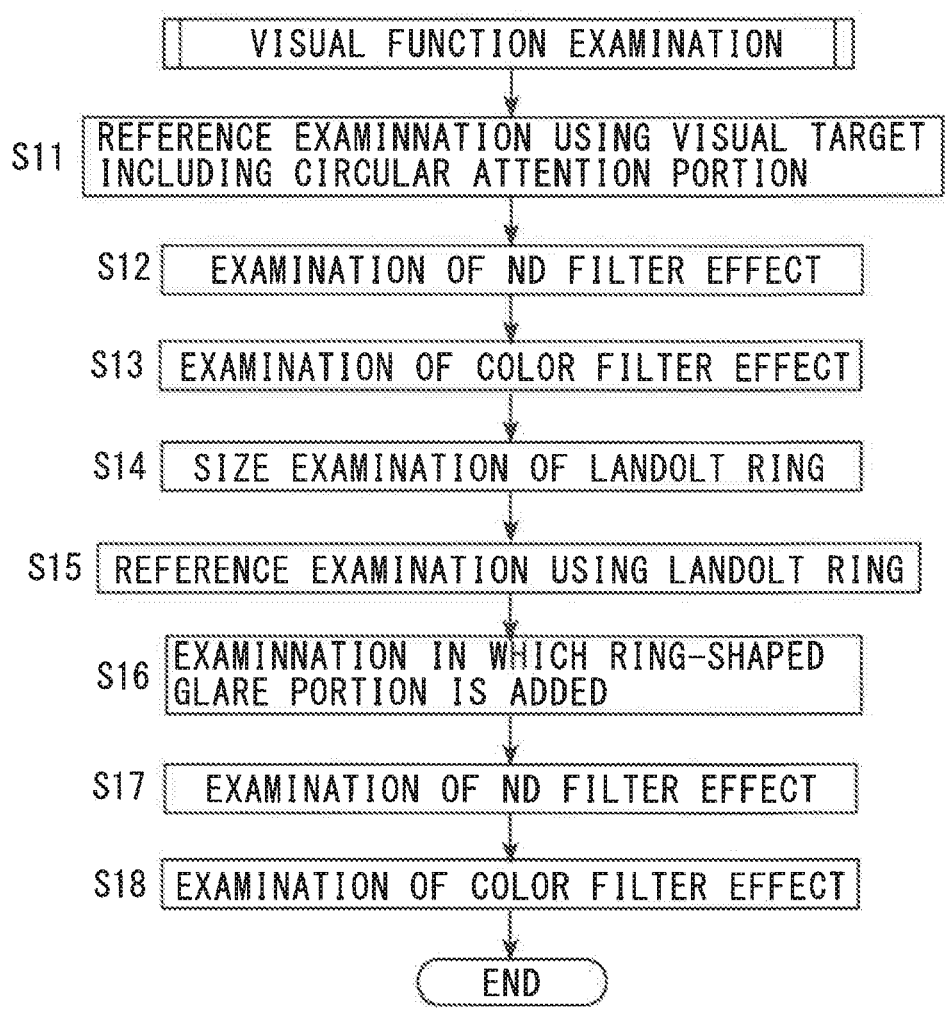
FIG. 5 is a flow chart (continued from FIG. 4) indicating the operation of the visual function examination system of the embodiment.

Note that in the visual function examination in step S1 (more specifically, in steps S11 to S13, and steps S15 to S18 in FIG. 5), the visual targets in which at least one in a combination of the luminance contrast value, the luminance average value, and the stimulus values of the color stimulus of the visual target is different, are sequentially presented to the subject. Further, the visual targets used in step S11 and step S12 are visual targets in which the luminance contrast value and the luminance average value are different. The same applies to step S16 and step S17. Further, in step S13 and step S18 in the visual function examination in step S1, the visual targets with the same combination of the stimulus values of the color stimulus are sequentially presented to the subject, and then the visual targets in which the combination of the stimulus values of the color stimulus is different from that of the previously presented visual targets are sequentially presented to the subject.

Further, as a modified example of the above-described visual function examination, it is also possible to configure such that the examination is performed by not only setting the brightness to 50% which is exemplified above but also changing the brightness in a plurality of stages in the examination of the ND filter effect. Further, in the examination of the color filter effect, any number of combinations of the stimulus values of the color stimulus may be employed. Further, each order of presentation of the visual targets may be the order of change from a state with a large luminance contrast value to a state with a small luminance contrast value, or from a state with a small luminance contrast value to a state with a large luminance contrast value. Further, although the example in which the examination is performed in the order of the reference examination, the examination of the ND filter effect, and the examination of the color filter effect, in the visual function examination in step S1 is described, but, it is also possible that the luminance contrast value is fixed, and the visual targets are sequentially presented in the order of A-0 in FIG. 6, A-N1 in FIG. 7, A-C1, A-C2, and A-C3 in FIG. 8. In this case, in the state of fixing the luminance contrast value, the reference examination, the examination of the ND filter effect, and the examination of the color filter effect (three types of examinations) are performed. Besides, it is also possible to sequentially present visual targets in which the combination of the luminance contrast value, the luminance average value, and the stimulus values of the color stimulus of the visual target is changed randomly.

The analysis part 23 in step S2 first calculates the luminance contrast value and the luminance average value based on the results of the visual function examination in step S1 (more specifically, in steps S11, S12, S13, and S15 to S18 in FIG. 5), and performs plotting on the CA diagram. Concretely, the analysis part 23 generates a luminance image of the visual target which is stored in the examination result storage part 22 as the result of the visual function examination. Subsequently, the analysis part 23 performs a convolution operation using a matrix on the luminance image, and then calculates the luminance contrast value and the luminance average value. Details of the operation will be omitted since they are disclosed in detail in the aforementioned Japanese Patent No. 3963299.

Figure 14:
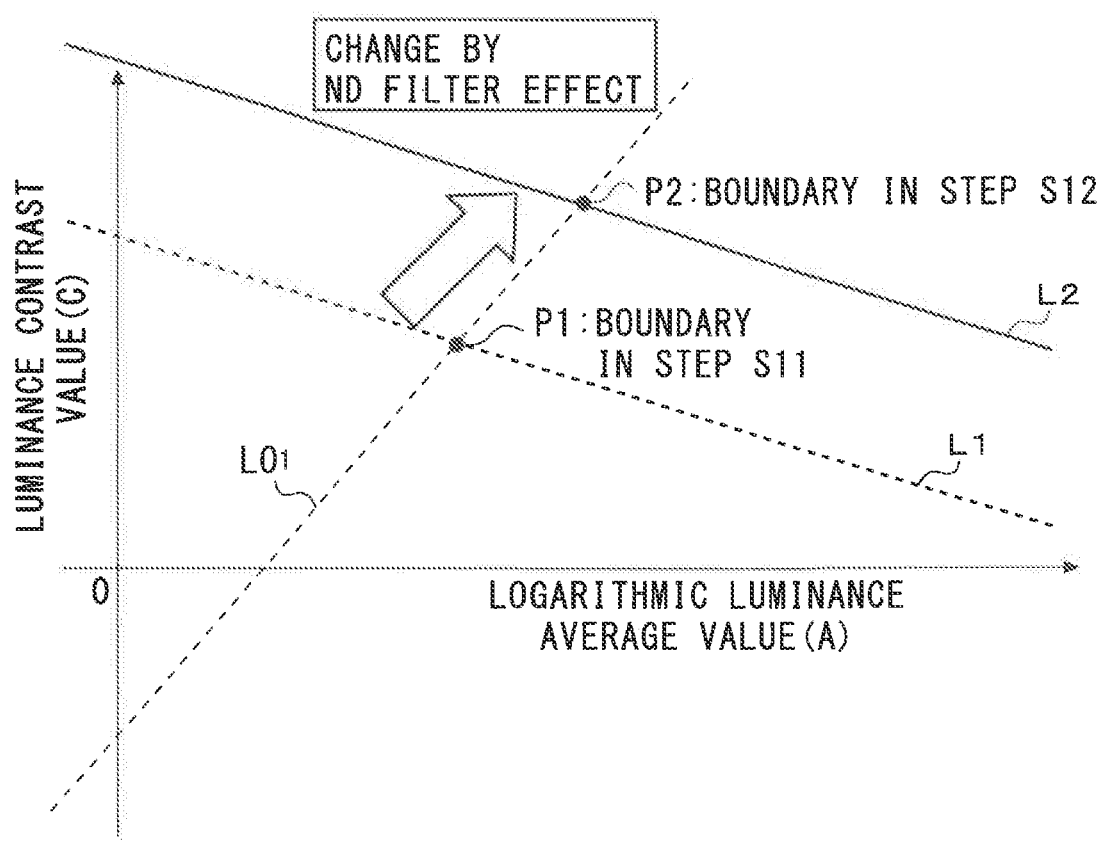
FIG. 14 is a diagram explaining a CA diagram of the embodiment.

FIG. 14 illustrates a CA diagram based on the results in steps S11 and S12 in FIG. 5. A point P1 indicates a plotted result of the reference examination in step S11. The point P1 indicates a boundary at which the subject does not feel the glare when the brightness of the circular attention portion is made to be sequentially brighter. When this point P1 is plotted, a boundary line L1 is determined on the CA diagram. The boundary line L1 is a predetermined straight line passing through the point P1, and is determined by methods of experiments and operations. As a basis for determining the boundary line L1, there can be cited the study reported in Summaries of technical papers of annual meeting (Kanto district) 40200, Architectural Institute of Japan, 2015. The same applies to the boundary line L1 and subsequent respective boundary lines. Further, in FIG. 14, a region below the boundary line L1 on the CA diagram is a region where the subject has the visibility, and a region above the boundary line L1 is a region where the subject does not have the visibility.

A point P2 indicates a plotted result of the examination of the ND filter effect in step S12. The point P2 indicates a boundary at which the subject does not feel the glare when the brightness of the circular attention portion is made to be sequentially brighter in the examination of the ND filter effect in step S12. Note that the point P1 and the point P2 exist on a straight line $L0_1$, as illustrated in FIG. 14. When this point P2 is plotted, a boundary line L2 is determined on the CA diagram. The boundary line L2 can be determined by shifting the boundary line L1 in parallel so that the boundary line L1 passes through the point P2. Note that it is also possible that when determining the boundary line L2, an inclination or a shape of the boundary line L1 is entirely or partially corrected in accordance with the parallel shift of the boundary line L1. Further, in FIG. 14, a region below the boundary line L2 on the CA diagram is a region where the subject has the visibility, and a region above the boundary line L2 is a region where the subject does not have the visibility. As illustrated in FIG. 14, if the reference examination using the visual target including the circular attention portion in step S11 is set to the control, in the result of the examination of the ND filter effect in step S12, the region where the subject has the visibility is changed, and the visibility of the subject is changed by the ND filter effect. Note that an arrow mark in FIG. 14 indicates an example in which the visibility of the subject is improved.

Figure 15:
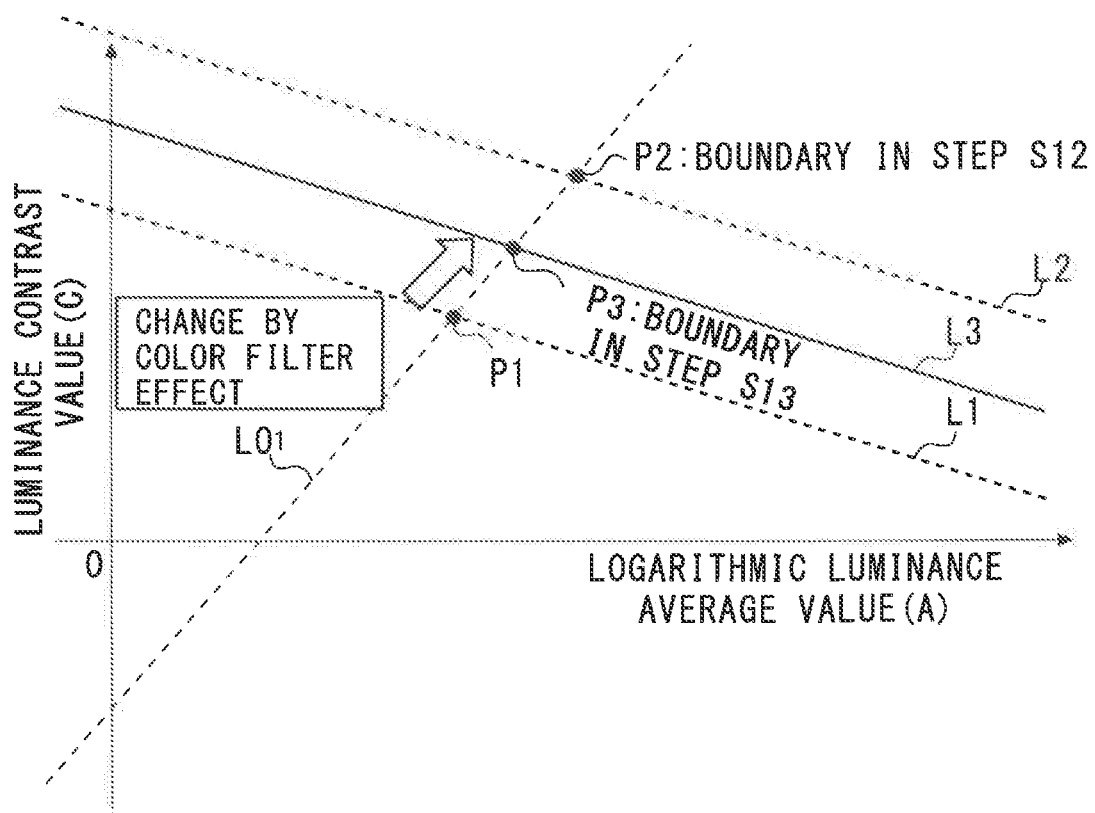
FIG. 15 is another diagram explaining the CA diagram of the embodiment.

FIG. 15 illustrates a CA diagram based on the result in step S13, in addition to the results in steps S11 and S12 in FIG. 5. The point P1, the point P2, the boundary line L1, and the boundary line L2 are the same as those of FIG. 14. A point P3 indicates a plotted result with the highest effect among the results of the examination of the color filter effect in step S13. In step S13, the three types of visual targets with different combinations of the stimulus values of the color stimulus are used to perform the examination. Based on the examination result indicating, among the above visual targets, the visual target with the highest effect, namely, the visual target in which the brightness of the attention portion regarding which the glare is felt is the highest, the above-described point P3 is plotted. The point P3 indicates a boundary at which the subject does not feel the glare when the brightness of the circular attention portion is made to be sequentially brighter in the examination of the color filter effect in step S13. Note that the point P3 also exists on the straight line $L0_1$, similarly to the point P1 and the point P2. When this point P3 is plotted, a boundary line L3 is determined on the CA diagram. The boundary line L3 can be determined by shifting the boundary line L1 in parallel so that the boundary line L1 passes through the point P3. Note that it is also possible that when determining the boundary line L3 as well, the inclination or the shape of the boundary line L1 is entirely or partially corrected in accordance with the parallel shift of the boundary line L1. Further, in FIG. 15, a region below the boundary line L3 on the CA diagram is a region where the subject has the visibility, and a region above the boundary line L3 is a region where the subject does not have the visibility. As illustrated in FIG. 15, if the reference examination using the visual target including the circular attention portion in step S11 Is set to the control, in the result of the examination of the color filter effect in step S13, the region where the subject has the visibility is changed, and the visibility of the subject is changed by the color filter effect. Note that an arrow mark in FIG. 15 indicates an example in which the visibility of the subject is improved.

Figure 16:
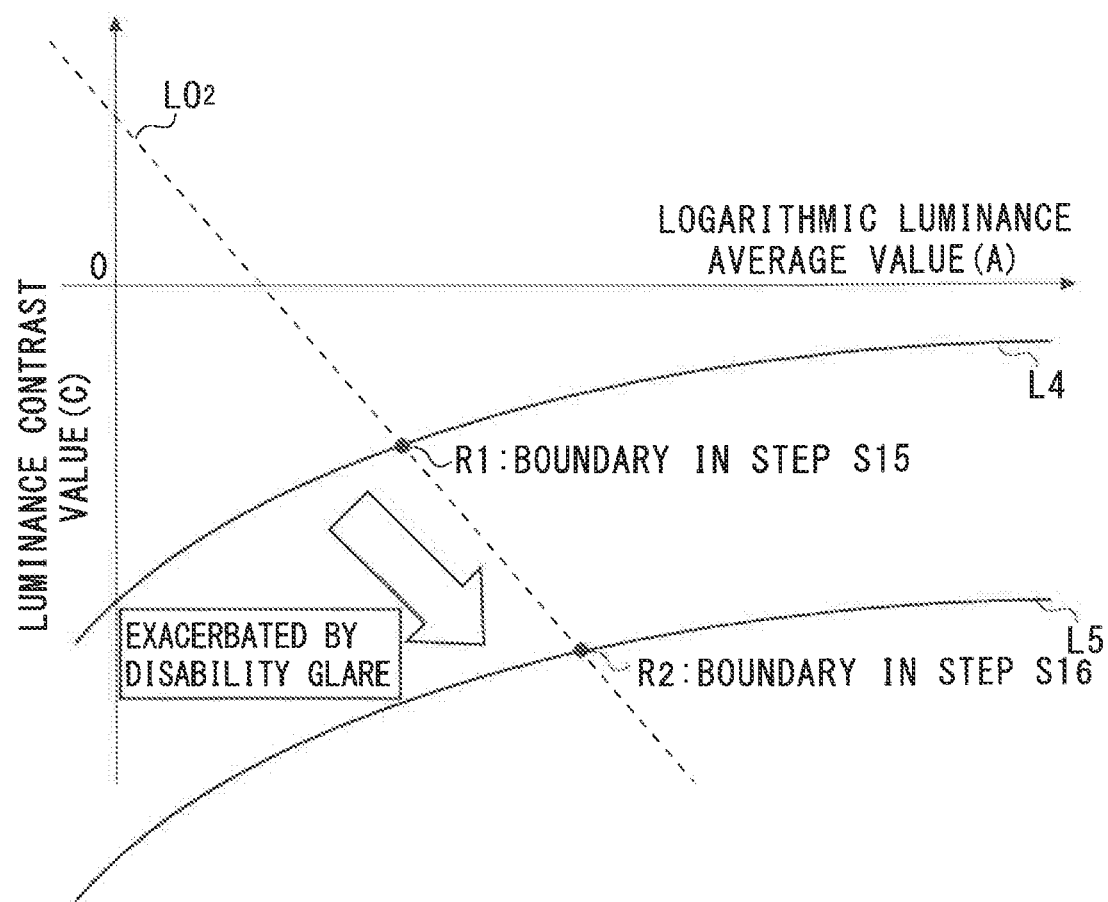
FIG. 16 is another diagram explaining the CA diagram of the embodiment.

FIG. 16 illustrates a CA diagram based on the results in steps S15 and S16 in FIG. 5. A point R1 indicates a plotted result of the reference examination using the Landolt ring B in step S15. The point R1 indicates a boundary at which the subject cannot visually recognize the visual target when the brightness of the Landolt ring B is made to be sequentially darker. When this point R1 is plotted, a boundary line L4 is determined on the CA diagram. As a basis for determining the boundary line L4, there can be cited the study reported in Summaries of technical papers of annual meeting (Kanto district) 40238, Architectural Institute of Japan, 2015. Further, in FIG. 16, a region below the boundary line L4 on the CA diagram is a region where the subject has the visibility, and a region above the boundary line L4 is a region where the subject does not have the visibility.

A point R2 indicates a plotted result of the reference examination in which the ring-shaped glare portion is added in step S16. The point R2 indicates a boundary at which the subject cannot visually recognize the visual target when the brightness of the Landolt ring B is made to be sequentially darker in the examination in step S16. Note that the point R1 and the point R2 exist on a straight line $L0_2$, as illustrated in FIG. 16. When this point R2 is plotted, a boundary line L5 is determined on the CA diagram. The boundary line L5 can be determined by shifting the boundary line L4 in parallel so that the boundary line L4 passes through the point R2. Note that it is also possible that when determining the boundary line L5 as well, an inclination or a shape of the boundary line L4 is entirely or partially corrected in accordance with the parallel shift of the boundary line L4. Further, in FIG. 16, a region below the boundary line L5 on the CA diagram is a region where the subject has the visibility, and a region above the boundary line L5 is a region where the subject does not have the visibility. As illustrated in FIG. 16, if the reference examination using the Landolt ring B in step S15 is set to the control, in the result of the reference examination in which the ring-shaped glare portion is added in step S16, the region where the subject has the visibility is reduced, and the visibility of the subject deteriorates.

Figure 17:
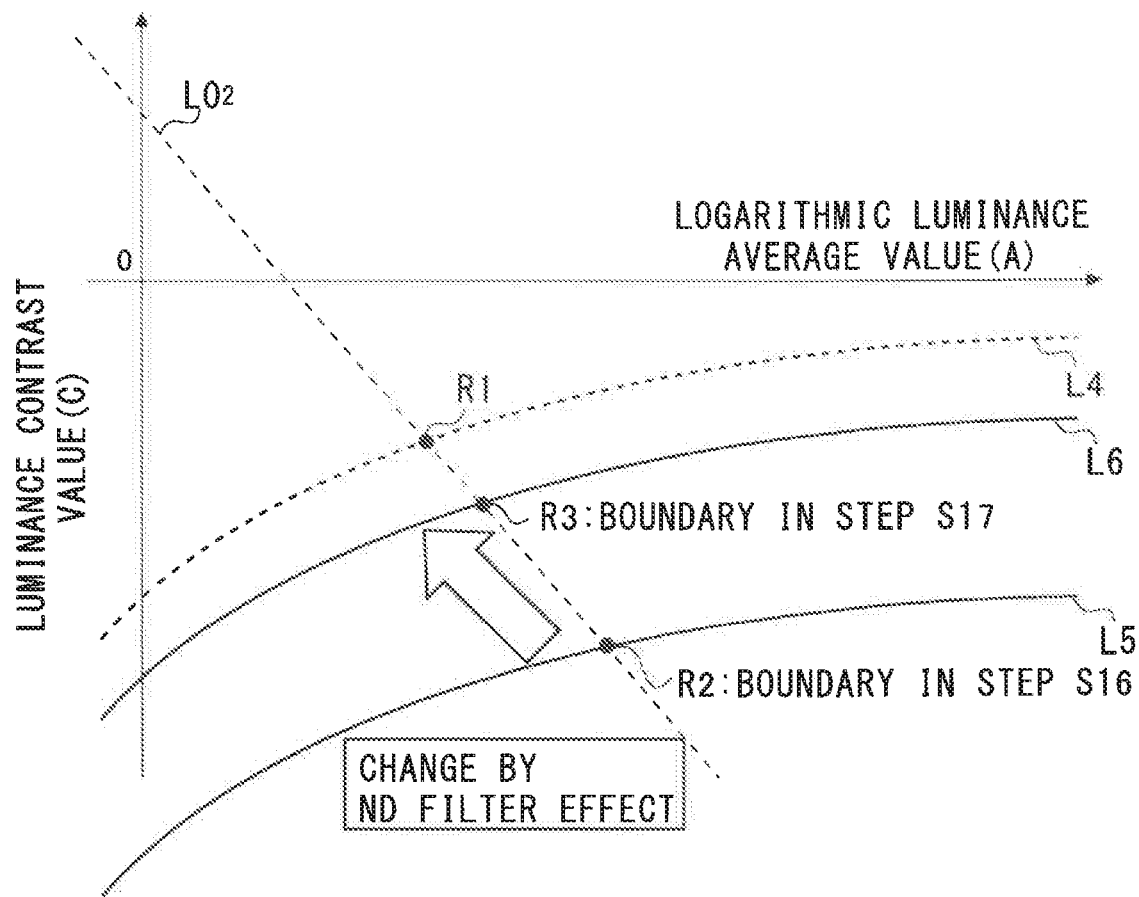
FIG. 17 is another diagram explaining the CA diagram of the embodiment.

FIG. 17 illustrates a CA diagram based on the result in step S17, in addition to the results in steps S15 and S16 in FIG. 5. The point R1, the point R2, the boundary line L4, and the boundary line L5 are the same as those of FIG. 16. A point R3 indicates a boundary at which the subject cannot visually recognize the visual target when the brightness of the Landolt ring B is made to be sequentially darker in the examination of the ND filter effect in step S17. Note that the point R3 also exists on the straight line $L0_2$, as illustrated in FIG. 17. When this point R3 is plotted, a boundary line 16 is determined on the CA diagram. The boundary line L6 can be determined by shifting the boundary line L4 in parallel so that the boundary line L4 passes through the point R3. Note that it is also possible that when determining the boundary line L6 as well, the inclination or the shape of the boundary line L4 is entirely or partially corrected in accordance with the parallel shift of the boundary line L4. Further, in FIG. 17, a region below the boundary line L6 on the CA diagram is a region where the subject has the visibility, and a region above the boundary line L6 is a region where the subject does not have the visibility. As illustrated in FIG. 17, if the reference examination using the visual target to which the ring-shaped glare portion is added in step S16 is set to the control, in the result of the examination of the ND filter effect in step S17, the region where the subject has the visibility is changed, and the visibility of the subject is changed by the ND filter effect. Note that an arrow mark in FIG. 17 indicates an example in which the visibility of the subject is improved.

Figure 18:
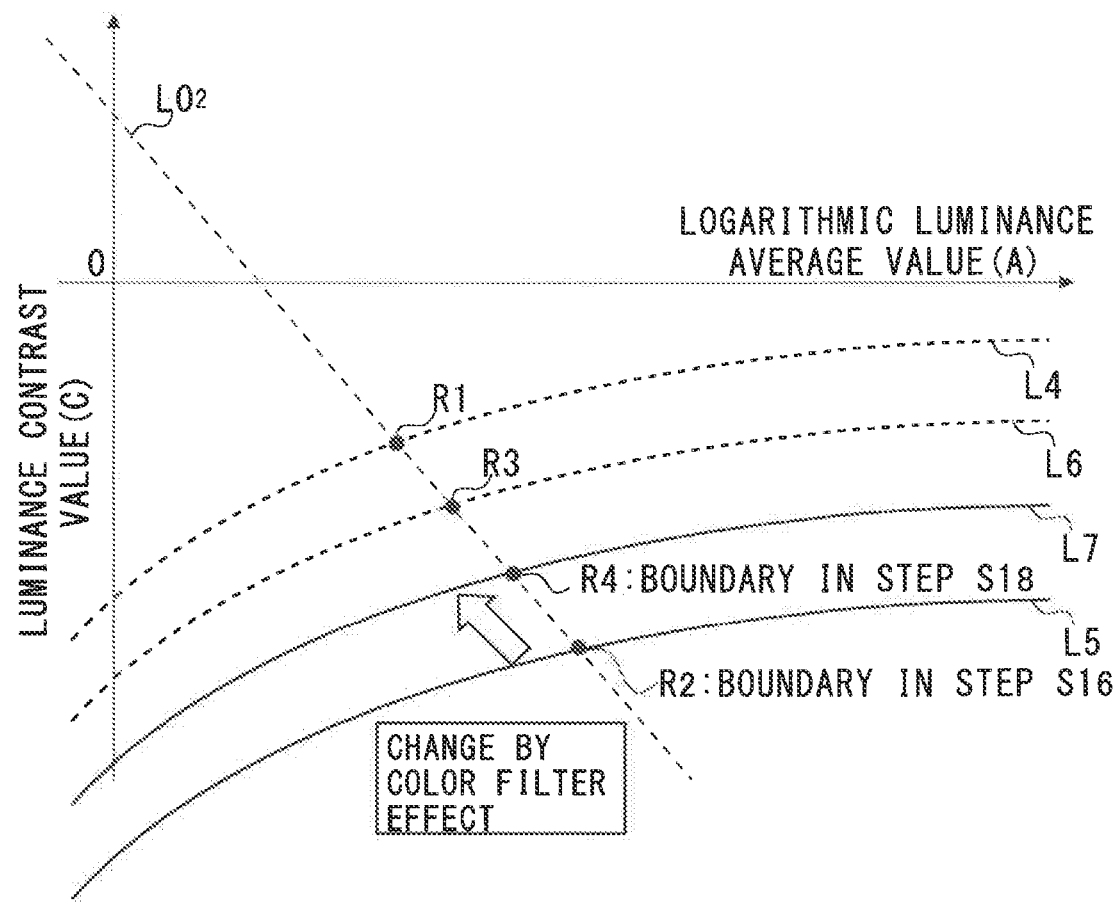
FIG. 18 is another diagram explaining the CA diagram of the embodiment.

FIG. 18 illustrates a CA diagram based on the result in step S18, in addition to the results in steps S15 to S17 in FIG. 5. The point R1, the point R2, the point R3, the boundary line L4, the boundary line L5, and the boundary line L6 are the same as those of FIG. 17. A point R4 indicates a plotted result with the highest effect among the results of the examination of the color filter effect in step S18. In step S18, the three types of visual targets with different combinations of the stimulus values of the color stimulus are used to perform the examination. Among the above, based on the examination result with the highest effect, namely, the examination result indicating that the brightness of the Landolt ring B capable of being visually recognized is the lowest (darkest), the above-described point R4 is plotted. The point R4 indicates a boundary at which the subject cannot visually recognize the visual target when the brightness of the Landolt ring B is made to be sequentially darker in the examination of the color filter effect in step S18. Note that the point R4 also exists on the straight line L02, as illustrated in FIG. 18. When this point R4 is plotted, a boundary line L7 is determined on the CA diagram. The boundary line L7 can be determined by shifting the boundary line L4 in parallel so that the boundary line L4 passes through the point R4. Note that it is also possible that when determining the boundary line L7 as well, the inclination or the shape of the boundary line L4 is entirely or partially corrected in accordance with the parallel shift of the boundary line L4. Further, in FIG. 18, a region below the boundary line L7 on the CA diagram is a region where the subject has the visibility, and a region above the boundary line L7 is a region where the subject does not have the visibility. As illustrated in FIG. 18, if the reference examination in which the ring-shaped glare portion is added in step S16 is set to the control, in the result of the examination of the color filter effect in step S18, the region where the subject has the visibility is changed, and the visibility of the subject is changed by the color filter effect. Note that an arrow mark in FIG. 18 indicates an example in which the visibility of the subject is improved.

It is also possible that the analysis part 23 displays the CA diagram explained by using FIG. 14 to FIG. 18 on the monitor 19 via the input and output I/F 16. By displaying such a CA diagram on the monitor 19, it is possible to visually present the results of the visual function examination to the examiner and the subject.

In step S3, the CPU 14 makes the optical characteristic calculation part 24 calculate the optical characteristic. As the optical characteristic, the X value, the Y value, the Z value, L*a*b*, or the like can be cited.

In the present embodiment, the optical characteristic of a lens for eyeglass as an optical member for compensating the visual function of the subject is determined as described above. The X value, the Y value, and the Z value are one of a color system defined by the CIE (Commission Internationale de l'Eclairage), and used as one of evaluation values indicating the optical characteristic of the optical lens in this case.

The optical characteristic calculation part 24 first selects the visual target to be an origin of the calculation of the optical characteristic, based on the result of the visual function examination in step S1. As described above, in the visual function examination in step S1, the examination results in seven pieces of processing of step S11, step S12, step S13, step S15, step S16, step S17, and step S18 are stored in the examination result storage part 22. The selection of the examination result used for the calculation of the optical characteristic may be performed in any way. For example, the optical characteristic calculation part 24 may select the examination result in which the region where the subject has the visibility is the largest on the CA diagram explained in FIG. 14 to FIG. 18. After that, the optical characteristic calculation part 24 may select the examination result in accordance with the purpose of use of the subject. In the description hereinbelow, a case where the optical characteristic is calculated based on the visual target whose stimulus value of B is set to 50% (whose color is yellow) in the examination of the color filter effect in step S18, will be explained as one example.

After selecting the visual target to be the origin of the calculation of the optical characteristic, the optical characteristic calculation part 24 determines a spectral distribution of a light source corresponding to the visual target. Here, the light source indicates one that generates light, and includes not only a light emitter such as an electric bulb or the sun but also reflected light. In the present embodiment, the monitor 19 corresponds to the light source, and the spectral distribution of the light source corresponding to the visual target can be determined by a spectral distribution of the monitor 19 at the time of presenting the visual target.

Figure 19:
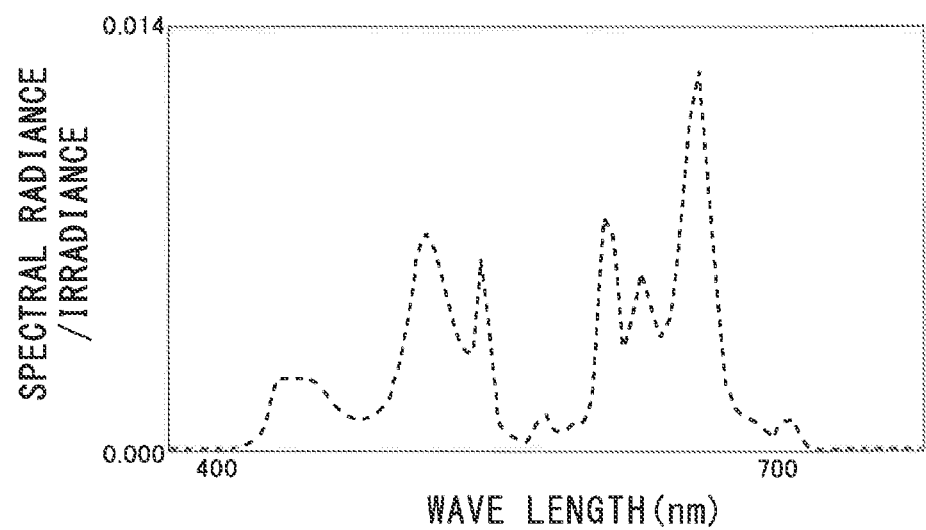
FIG. 19 is a diagram explaining a spectral distribution of a light source of the embodiment.
Figure 20:
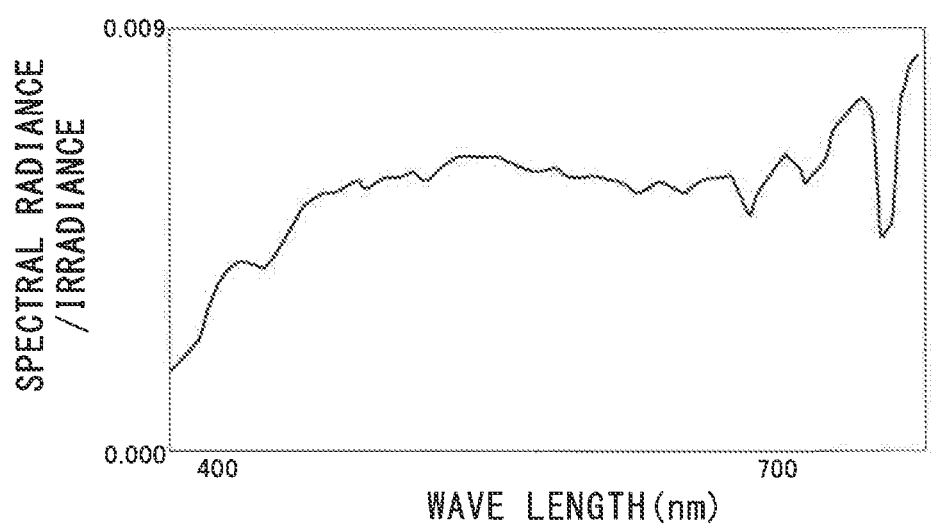
FIG. 20 is another diagram explaining a spectral distribution of a light source of the embodiment.
Figure 21:
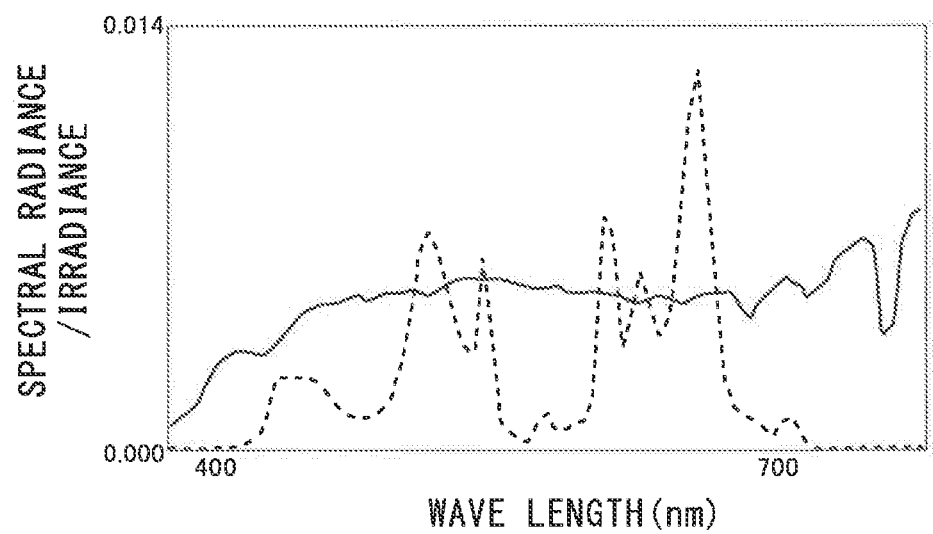
FIG. 21 is another diagram explaining the spectral distributions of the light sources of the embodiment.

FIG. 19 illustrates a spectral distribution of the monitor 19 when displaying the visual target whose stimulus value of B is set to 50% (whose color is yellow) among the visual targets stored as the examination results in the examination result storage part 22 in the examination of the color filter effect in step S18 (the spectral distribution is referred to as a spectral distribution A, hereinafter). Further, FIG. 20 illustrates a spectral distribution of a light source which is dominant in an environment where the subject wants to perform visual recognition (the spectral distribution is referred to as a spectral distribution B, hereinafter). Note that FIG. 20 illustrates a spectral distribution of a certain light source as one example. Further, FIG. 21 illustrates a diagram in which the two spectral distributions are illustrated. Note that in each of FIG. 19 to FIG. 21, a horizontal axis indicates a wavelength of light, and a vertical axis indicates a spectral radiance or a spectral irradiance in each wavelength.

Figure 22:
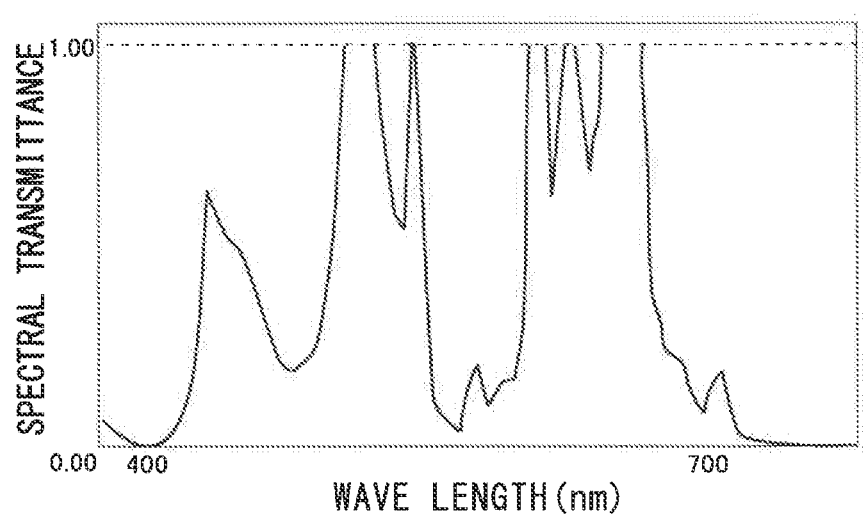
FIG. 22 is a diagram explaining a spectral transmittance of the embodiment.

The optical characteristic calculation part 24 calculates a spectral transmittance for converting the spectral distribution B to the spectral distribution A. Here, the spectral transmittance Indicates a spectral concentration ratio between a spectral concentration of a transmitted luminous flux and a spectral concentration of an incident luminous flux. The optical characteristic calculation part 24 determines (numeric value of vertical axis of spectral distribution A)/(numeric value of vertical axis of spectral distribution B) for each wavelength of light at predetermined intervals, to thereby calculate the spectral transmittance for each wavelength of light. Note that the interval of the wavelength of light for calculating the spectral transmittance may be an equal interval or may be a non-equal interval. For example, it is possible that a detailed spectral transmittance is calculated at a narrow interval of wavelength regarding a wavelength band which is regarded as important by the subject, and regarding a wavelength band other than that, a rough spectral transmittance is calculated at a wide interval of wavelength. FIG. 22 illustrates one example of the calculated spectral transmittance. Note that an upper limit value of the spectral transmittance is set to 1.00, and when the calculated spectral transmittance exceeds 1.00, the calculation result is replaced with 1.00. Subsequently, the optical characteristic calculation part 24 calculates the X value, the Y value, and the Z value corresponding to this spectral transmittance.

Note that when determining a wavelength dependency of the spectral transmittance of the optical member for compensating the visual function of the subject, the optical characteristic calculation part 24 may perform processing in which an assumption is set such that a region of the wavelength is formed of three wavelength regions corresponding to main emission wavelength regions of respective lights of R, G, and B of the visual target, and further, respective transmittance average values in the three wavelength regions are defined as numeric values same as the respective stimulus values of R, G, and B of the visual target.

The CPU 14 makes the optical characteristic calculation part 24 calculate the X value, the Y value, and the Z value, and then terminates the series of processing.

As described above, according to the first embodiment, the visual function examination is performed by sequentially presenting to the subject the visual targets in which at least one in the combination of the luminance contrast value between the luminance of the attention portion and the luminance of the background portion, the luminance average value of the visual target including the attention portion and the background portion, and the stimulus values of the color stimulus of the visual target is different, and based on the examination result, the boundary between the region where the subject has the visibility and the region where the subject does not have the visibility is determined for each combination of the stimulus values of the color stimulus in the coordinate system indicating the correlation between the luminance contrast value and the luminance average value. Therefore, since a relationship between the optical characteristic of the optical member and the visibility can be estimated, it is possible to realize the visual function examination which takes various luminance conditions including one when performing the examination into consideration.

Further, according to the first embodiment, the visual target is displayed on the display device. Therefore, the subject is not required to try a plurality of optical lenses, and the visual function examination can be carried out in a relatively short period of time.

Second Embodiment

Hereinafter, a second embodiment of the present invention will be described by using the drawings. Note that hereinbelow, only a part which is different from that of the first embodiment will be described, and explanation regarding a part similar to that of the first embodiment will be omitted.

A visual function examination system of a second embodiment has a configuration similar to that of the visual function examination system of the first embodiment. However, the visual function examination system of the second embodiment acquires target information regarding the visibility of the subject, calculates a target value based on the acquired target information, and calculates the optical characteristic based on the calculated target value.

Figure 23:
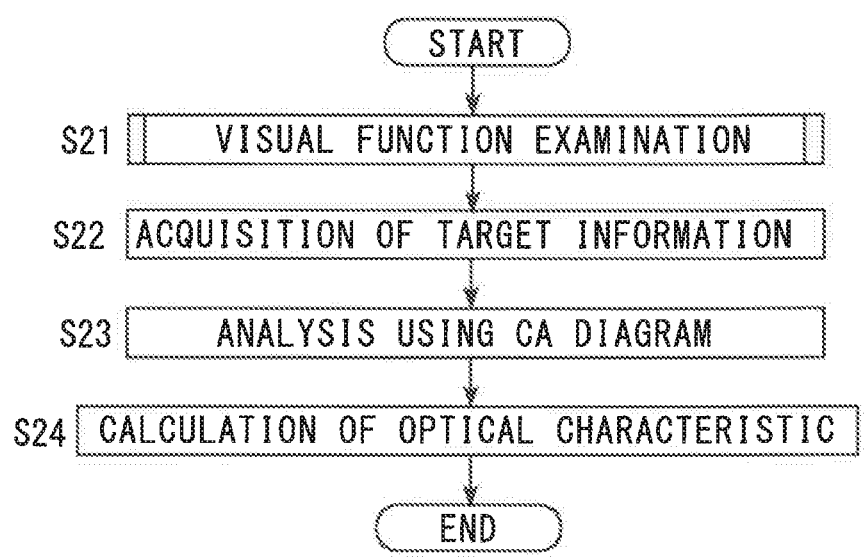
FIG. 23 is another flow chart indicating the operation of the visual function examination system of the embodiment.

An operation of the visual function examination system of the present embodiment will be described while referring to a flow chart illustrated in FIG. 23.

In step S21, the CPU 14 controls the respective parts to perform the visual function examination, similarly to step S1 in FIG. 4 described above (more specifically, steps S11 to S18 in FIG. 5).

In step S22, the CPU 14 acquires target information via an input and output I/F 18. The target information is information Indicating a light source in an environment which surrounds the subject. Concretely, there can be considered an image in which a place where the subject wants to perform visual recognition is photographed, an image in which a scene or a situation where the subject has a problem in the visibility or it can be estimated that the subject has a problem in the visibility is photographed, and the like. The scene or the situation where the subject has a problem in the visibility is, for example, a scene or a situation where the subject feels the glare or the darkness, the subject has difficulty in discriminating an attention portion such as a guide sign, the subject has difficulty in obtaining a stereognostic sense regarding an attention portion such as a pillar or stairs, and the like in dairy life. Similarly, the scene or the situation where it can be estimated that the subject has a problem in the visibility is a scene or a situation capable of being estimated based on experiments and hearing from the subject performed by a researcher, a health care worker and the like. In any of the above cases, by acquiring an image in which such a scene or a situation is previously photographed as the target information, it becomes possible to calculate the optical characteristic of the optical member in accordance with the visual function which is different for each subject. Note that each image may be photographed in any way, but, it is desirably an image capable of being converted or approximated to a luminance image (for example, an RGB image, a YCbCr image, or the like) in view of the application to the above-described CA diagram.

Further, the target information may be any information as long as it Indicates a light source in an environment which surrounds the subject, other than the above-described image. For example, there can be considered an evaluation value, a numeric value, or the like indicating a place where the subject wants to perform visual recognition, an evaluation value, a numeric value, or the like indicating a scene or a situation where the subject has a problem in the visibility or it can be estimated that the subject has a problem in the visibility. The evaluation value indicating the scene or the situation where the subject has a problem in the visibility is, for example, an illuminance or a luminance measured in a scene or a situation where the subject feels the glare or the darkness, the subject has difficulty in discriminating an attention portion such as a guide sign, the subject has difficulty in obtaining a stereognostic sense regarding an attention portion such as a pillar or stairs in dairy life. Similarly, the evaluation value indicating the scene or the situation where it can be estimated that the subject has a problem in the visibility is an illuminance or a luminance measured in a scene or a situation capable of being estimated based on experiments and hearing from the subject performed by a researcher, a health care worker and the like. In any of the above cases, by acquiring an evaluation value which is previously measured in such a scene or a situation as the target information, it becomes possible to calculate the optical characteristic of the optical member in accordance with the visual function which is different for each subject. Note that each evaluation value may be measured or calculated in any way, but, it is desirably an evaluation value capable of being converted or approximated to a luminance contrast value and a luminance average value (for example, an illuminance, a luminance, or the like) in view of the application to the above-described CA diagram.

In step S23, the CPU 14 makes the analysis part 23 perform an analysis by using the CA diagram. Details of the CA diagram are similar to those of the first embodiment.

The analysis part 23 first calculates a target value based on the target information acquired in step S22. The target value is a luminance contrast value and a luminance average value corresponding to the target information. When the target information is an image, the analysis part 23 converts or approximates the image to a luminance image. For example, when the target information is an RGB image, the analysis part 23 uses a publicly-known method to convert the image of RGB color system to an image of XYZ color system, and sets a Y image to a luminance image. Subsequently, the analysis part 23 sets an attention portion and a background portion in the luminance image, and calculates a luminance contrast value and a luminance average value based on luminance values of those regions.

Meanwhile, when the target information is an evaluation value, the analysis part 23 converts or approximates the evaluation value to a luminance contrast value and a luminance average value. For example, when the target information is an illuminance, the analysis part 23 uses a publicly-known equation to convert the illuminance to a luminance, and after that, it sets a ratio between a luminance of an attention portion and a luminance of a background portion to a luminance contrast value, and sets an average value of the luminance of the attention portion and the luminance of the background portion to a luminance average value.

Figure 24:
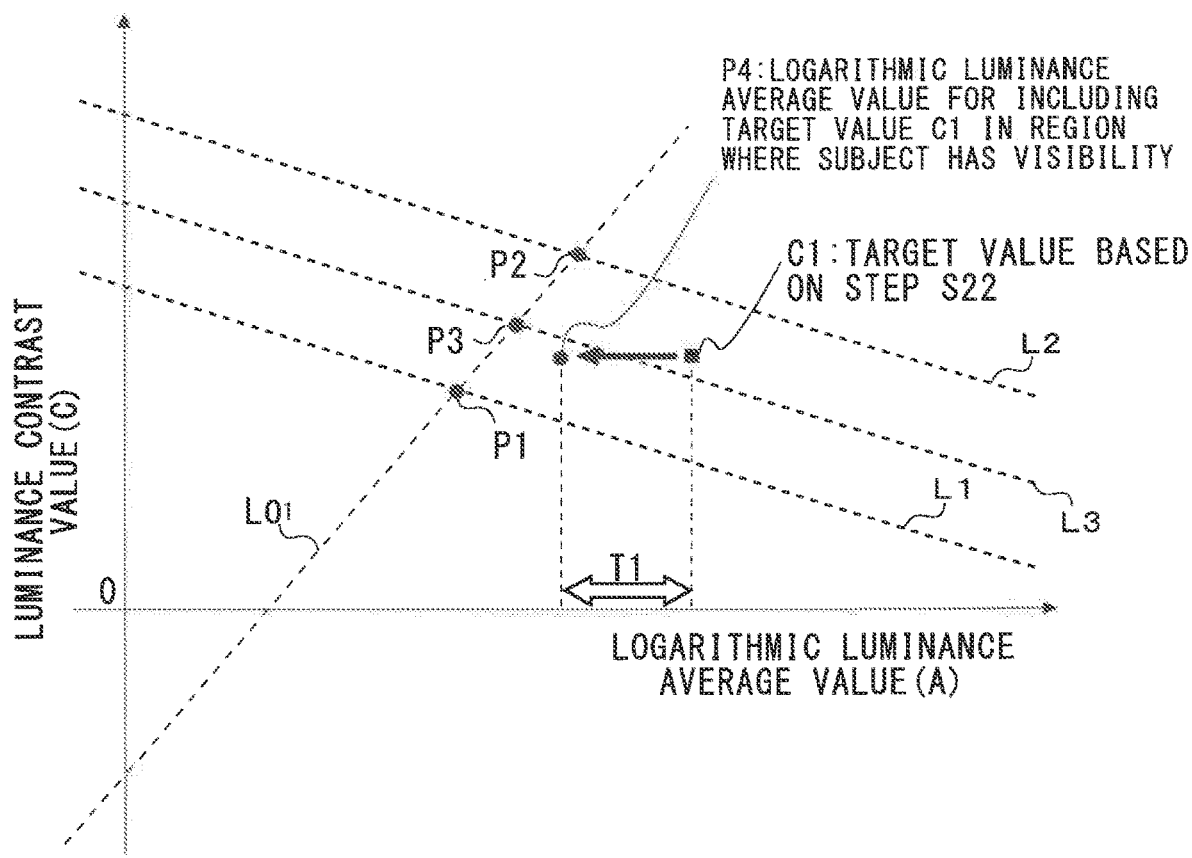
FIG. 24 is another diagram explaining the CA diagram of the embodiment.

FIG. 24 illustrates a CA diagram based on the result of the visual function examination when the visibility examination which supposes the discomfort glare is performed in step S21. The point P1, the point P2, the point P3, the boundary line L1, the boundary line L2, and the boundary line L3 are the same as those of FIG. 15 in the first embodiment. A point C1 Indicates the above-described target value (the luminance contrast value and the luminance average value) plotted on the CA diagram. The point C1 indicates a point where the subject wants the visibility on the CA diagram.

Figure 25:
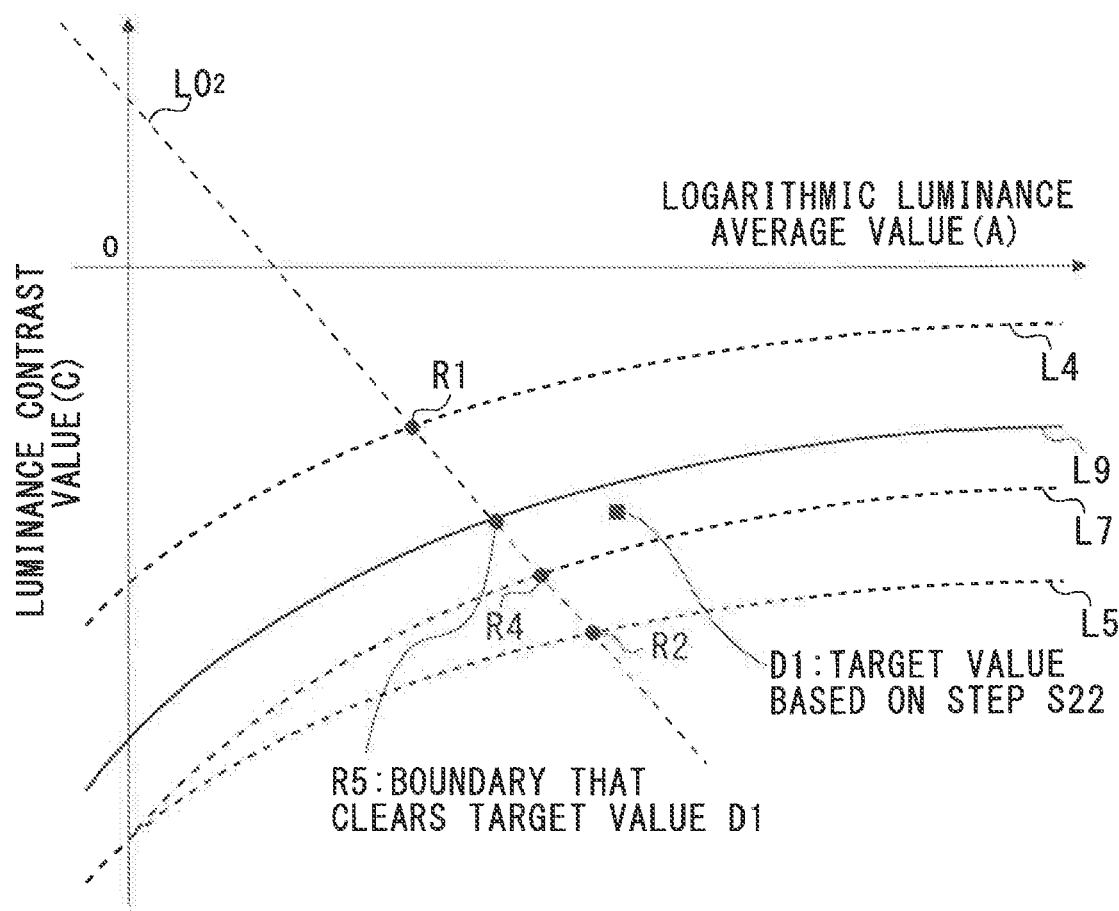
FIG. 25 is another diagram explaining the CA diagram of the embodiment.

Meanwhile, FIG. 25 illustrates another CA diagram based on the result of the visual function examination when the visibility examination which supposes the disability glare is performed in step S21. The point R1, the point R2, the point R4, the boundary line L4, the boundary line L5, and the boundary line L7 are the same as those of FIG. 16 in the first embodiment. A point D1 Indicates the above-described target value (the luminance contrast value and the luminance average value) plotted on the CA diagram. The point D1 indicates a point where the subject wants the visibility on the CA diagram.

In step S24, the CPU 14 makes the optical characteristic calculation part 24 calculate the optical characteristic (the X value, the Y value, and the Z value, for example).

As illustrated in FIG. 24, when the visibility examination which supposes the discomfort glare is performed in step S21, the optical characteristic calculation part 24 shifts the point C1 corresponding to the target value (the luminance contrast value and the luminance average value) calculated in step S24 to a point P4 in a negative direction of the horizontal axis on the CA diagram so that the point C1 Is Included in the region having the visibility with respect to the boundary line L3. This point P4 becomes a boundary for making the point C1 corresponding to the target value to be included in the region where the subject has the visibility. Subsequently, the optical characteristic calculation part 24 determines the optical characteristic from this point P4. Concretely, the optical characteristic calculation part 24 first calculates a logarithmic luminance average difference T, namely, a luminance average value ratio between the point P4 and the point C1, and determines a spectral distribution of the visual target corresponding to the point P4 by multiplying a spectral distribution of the visual target corresponding to the point P3 by the ratio. After that, from the spectral distribution corresponding to the point P4, the optical characteristic can be determined through processing similar to that of the method described in the first embodiment.

When the visibility examination which supposes the disability glare is performed in step S21, the optical characteristic calculation part 24 determines a boundary line L9 on the CA diagram so that the point D1 corresponding to the target value (the luminance contrast value and the luminance average value) calculated in step S24 is included in the region having the visibility, as illustrated in FIG. 25. The boundary line L9 Is set when the boundary line L4 explained in the first embodiment is shifted in parallel so as to include the point D1 in the region having the visibility. Next, the optical characteristic calculation part 24 determines a point R5 at which the boundary line L9 and the straight line $L0_2$ explained in the first embodiment intersect, as illustrated in FIG. 25. This point R5 becomes a boundary for making the point D1 corresponding to the target value to be included in the region where the subject has the visibility. Subsequently, the optical characteristic calculation part 24 determines the optical characteristic from this point R5. Concretely, the optical characteristic calculation part 24 first calculates a luminance average value ratio between the point R5 and the point R4, and determines a spectral distribution of the visual target corresponding to the point R5 by multiplying a spectral distribution of the visual target corresponding to the point R4 by the ratio. After that, from the spectral distribution corresponding to the point R5, the optical characteristic can be determined through processing similar to that of the method described in the first embodiment.

Subsequently, the optical characteristic calculation part 24 calculates the X value, the Y value, and the Z value based on the spectral distribution of the light source similarly to the first embodiment, and then terminates the series of processing.

As described above, according to the second embodiment, the information indicating the light source in the environment that surrounds the subject is acquired as the target information regarding the visibility of the subject, and the target value in the coordinate system is calculated based on the target information. Subsequently, based on the examination result of the visual function examination and the calculated target value, the optical characteristic of the optical member is calculated. Therefore, by performing an analysis by plotting a condition of an object which the subject wants to visually recognize in real life on the CA diagram, it is possible to compensate the visual function of the subject, namely, it is possible to calculate the optical characteristic of the optical member which makes it possible to visually recognize the object which the subject wants to visually recognize.

Note that in the above-described respective embodiments, there can be considered various possibilities regarding the analysis in the CA diagram. For example, it is possible to simulate the visibility in the use environment by determining a spectral distribution of a light source which is dominant in an environment where the subject uses the optical member such as the optical lens, and using the spectral distribution for the calculation of the optical characteristic of the optical member. Further, since it is possible to generate the CA diagram for each optical characteristic of the optical member such as the optical lens, it is also possible to perform various simulations regarding the use.

Further, each of the visual targets described in the above-described respective embodiments is one example, and the present invention is not limited to this example. For instance, in the above-described respective embodiments, the circular portion or the Landolt ring is exemplified as the attention portion of the visual target, but, any shape may be employed such as a figure or a character other than that.

Further, in the above-described respective embodiments, the liquid crystal display device or the organic EL display device is exemplified as a concrete example of the monitor 19, but, the present invention is not limited to this example. Any display device may be employed as long as it already knows or it can measure a spectral distribution. For example, a display device having a light source with a color (Yellow, for example) other than three primary colors of RGB may also be employed. Further, it is also possible to employ a display device of backlight system, a self-luminous display device, or a display device of projection type.

Further, although the optical lens is exemplified as one example of the optical member in the above-described respective embodiments, the present invention is not limited to this example. For instance, it is also possible to employ a loupe-type optical lens, or a cover or a film which adjusts an amount of light which is incident from an Illumination, a window glass, and the like, as an optical member that controls a wavelength of light according to individuals. Further, it is also possible to employ a cover, a filter, or a film which is disposed on an object itself such as an illumination fixture, a display, or a window glass of a building, a vehicle, and the like. Further, the present invention can also be applied to a building material or a coating material for a floor, a wall, a ceiling, and the like, Further, although the above-described respective embodiments explain the visual function examination system which acquires the information regarding the optical member which compensates the visual function of the subject, it is also possible to employ application as follows.

Figure 26:
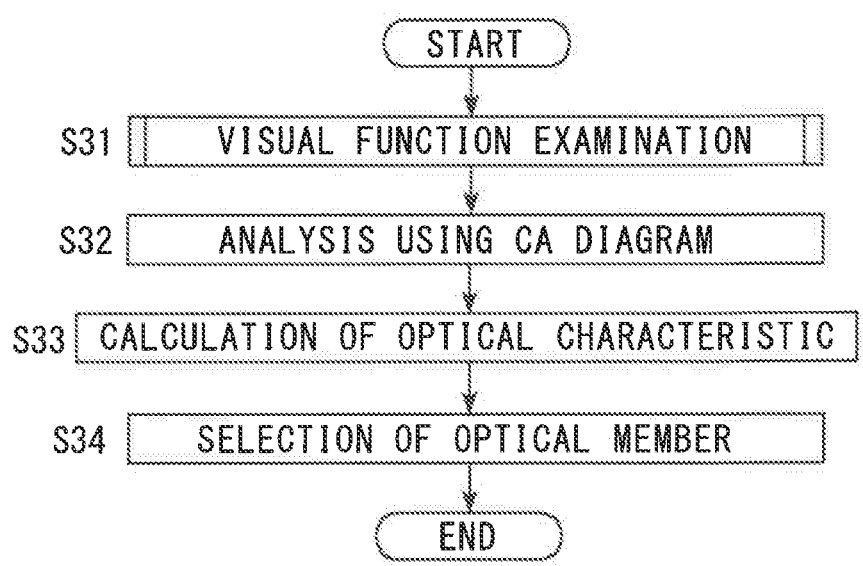
FIG. 26 is a flow chart indicating a selection method of an optical member of an embodiment.

For example, a selection method of an optical member in which an optical member which compensates the visual function of the subject is selected from a plurality of optical members with different characteristics based on the result of the visual function examination described in the above-described respective embodiments, is also effective as a concrete example of the present invention. FIG. 26 is a flow chart illustrating one example of a selection method of an optical member.

In respective processes of step S31 to step S33, processing similar to that of the respective processes of step S1 to step S3 in the above-described first embodiment is performed.

In step S34, the optical member is selected based on the optical characteristic (the X value, the Y value, the Z value, or L*a*b*, for example) calculated in step S33. For instance, a table in which a previously prepared optical characteristic (the X value, the Y value, and the Z value, for example) is made to correspond to previously prepared plural optical members, is referred to. Subsequently, the optical member whose optical characteristic corresponds to or is close to the optical characteristic (the X value, the Y value, the Z value, or L*a*b*, for example) calculated in step S33 is selected.

By the selection method of the optical member described above, it is possible to select the optical member which compensates the visual function of the subject.

Figure 27:
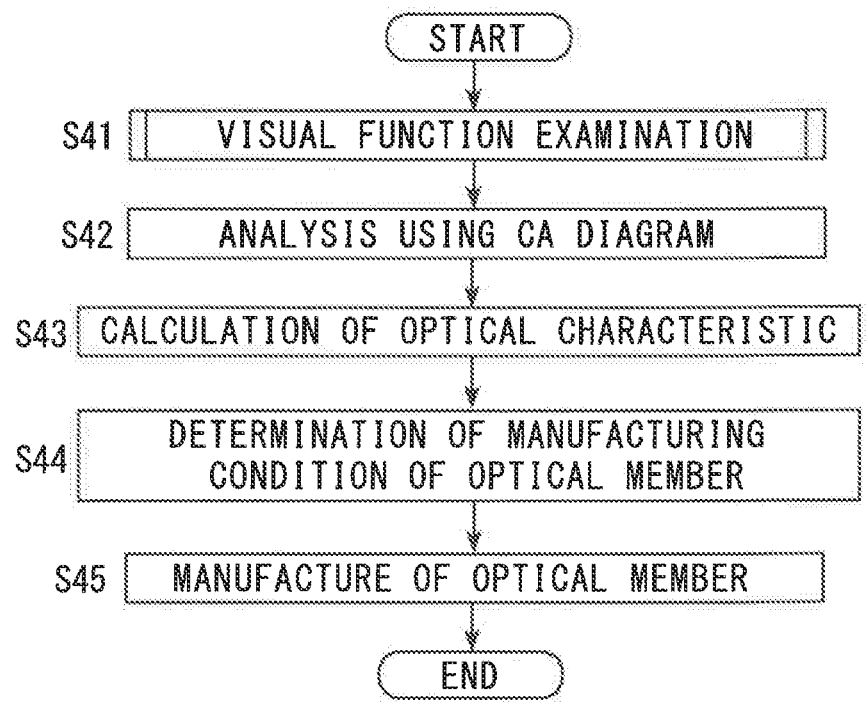
FIG. 27 is a flow chart indicating a manufacturing method of an optical member of an embodiment.

Further, a manufacturing method of an optical member in which an optical member which compensates the visual function of the subject is manufactured based on the result of the visual function examination described in the above-described respective embodiments, is also effective as a concrete example of the present invention. FIG. 27 is a flow chart illustrating one example of a manufacturing method of an optical member.

In respective processes of step S41 to step S43, processing similar to that of the respective processes of step S1 to step S3 in the above-described first embodiment is performed.

In step S44, a manufacturing condition of the optical member is determined based on an optical characteristic (the X value, the Y value, and the Z value, for example) calculated in step S43 or an optical characteristic close to the aforementioned optical characteristic.

In step S45, the optical member is manufactured in accordance with the manufacturing condition determined in step S44.

Through the manufacturing method of the optical member described above, it is possible to manufacture the optical member which compensates the visual function of the subject.

Figure 28:
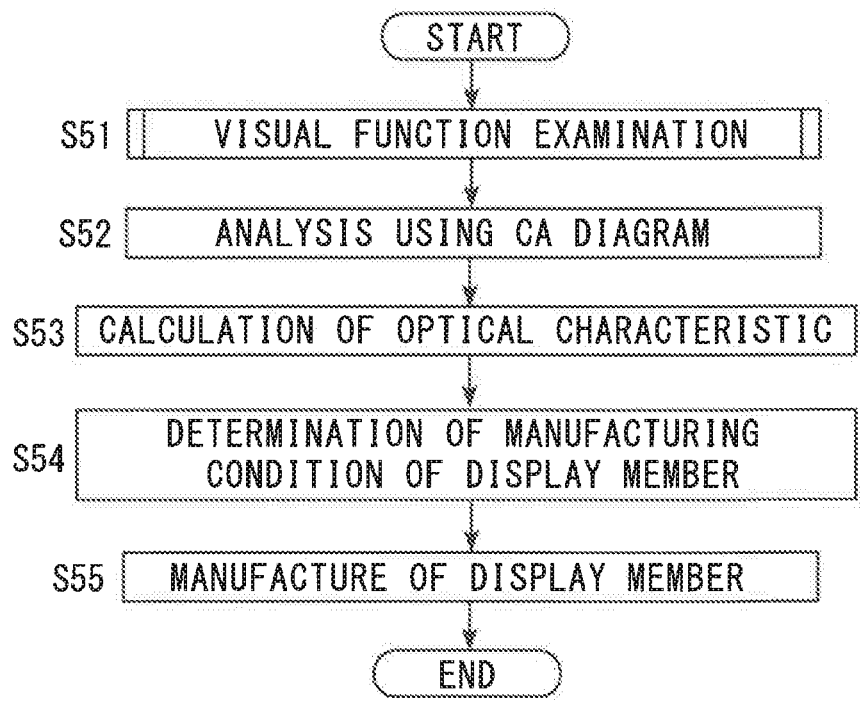
FIG. 28 is a flow chart indicating a manufacturing method of a display member of an embodiment.

Further, a manufacturing method of a display member in which a display member which compensates the visual function of the subject is manufactured based on the result of the visual function examination described in the above-described respective embodiments, is also effective as a concrete example of the present invention. Here, as the display member, there can be considered various monitors of a computer, a monitor of a smartphone or the like, a monitor of a tablet PC, a monitor or a television, a display of closed circuit TV (CCTV), a head mount display, or the like. FIG. 28 is a flow chart illustrating one example of a manufacturing method of a display member.

In respective processes of step S51 to step S53, processing similar to that of the respective processes of step S1 to step S3 in the above-described first embodiment is performed.

In step S54, a manufacturing condition of the display member is determined based on an optical characteristic (the X value, the Y value, and the Z value, for example) calculated in step S53 or an optical characteristic close to the aforementioned optical characteristic.

In step S55, the display member is manufactured in accordance with the manufacturing condition determined in step S54.

Through the manufacturing method of the display member described above, it is possible to manufacture the display member which compensates the visual function of the subject.

Figure 29:
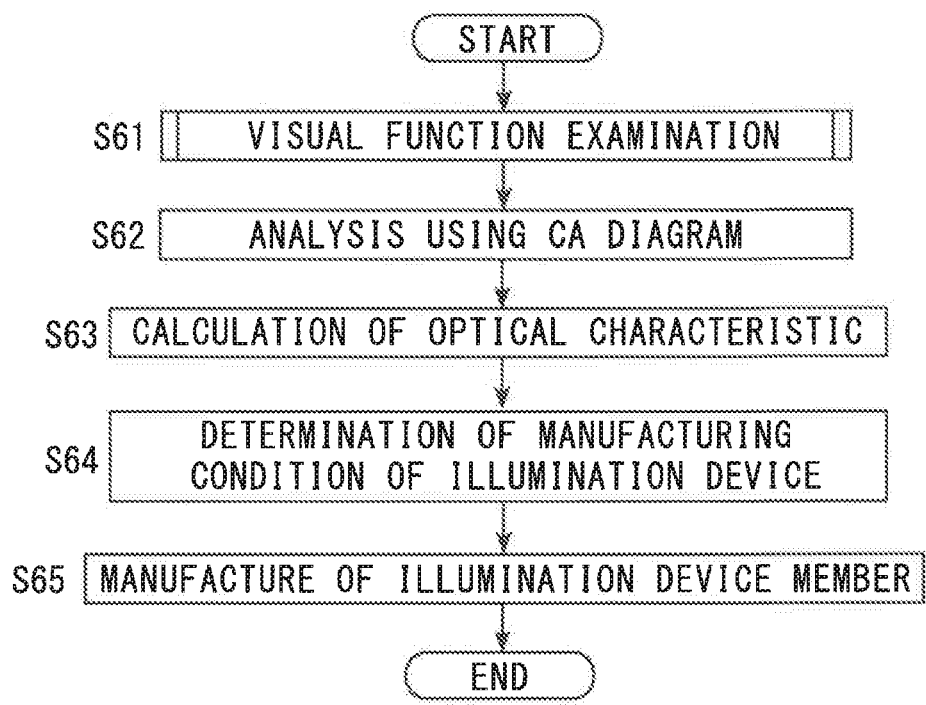
FIG. 29 is a flow chart indicating a manufacturing method of an illumination apparatus of an embodiment.

Further, a manufacturing method of an illumination apparatus in which an illumination apparatus which compensates the visual function of the subject is manufactured based on the result of the visual function examination described in the above-described respective embodiments, is also effective as a concrete example of the present invention. FIG. 29 is a flow chart illustrating one example of a manufacturing method of an illumination apparatus.

In respective processes of step S61 to step S63, processing similar to that of the respective processes of step S1 to step S3 in the above-described first embodiment is performed.

In step S64, a manufacturing condition of the illumination apparatus is determined based on an optical characteristic (the X value, the Y value, and the Z value, for example) calculated in step S63 or an optical characteristic close to the aforementioned optical characteristic.

In step S65, the illumination apparatus is manufactured in accordance with the manufacturing condition determined in step S64.

Through the manufacturing method of the illumination apparatus described above, it is possible to manufacture the illumination apparatus which compensates the visual function of the subject.

Note that although the example of calculating the optical characteristic (the X value, the Y value, and the Z value, for example) by performing the processing similar to that of the respective processes of step S1 to step S3 in the first embodiment is described in the flow charts of FIG. 26 to FIG. 29 described above, it is also possible to configure such that the optical characteristic (the X value, the Y value, and the Z value, for example) is calculated by performing the processing similar to that of the respective processes of step S21 to step S24 in the second embodiment.

Further, although the visual function examination system configured by the computer 11, the input device 18, and the monitor 19 is exemplified in the above-described respective embodiments, a visual function examination device in which the respective parts in the above-described respective embodiments are integrally manufactured, is also effective as a concrete example of the present invention. Further, an optical characteristic calculation device which calculates the optical characteristic based on the result of the visual function examination described in the above-described respective embodiments is also effective as a concrete example of the present invention.

Figure 30:
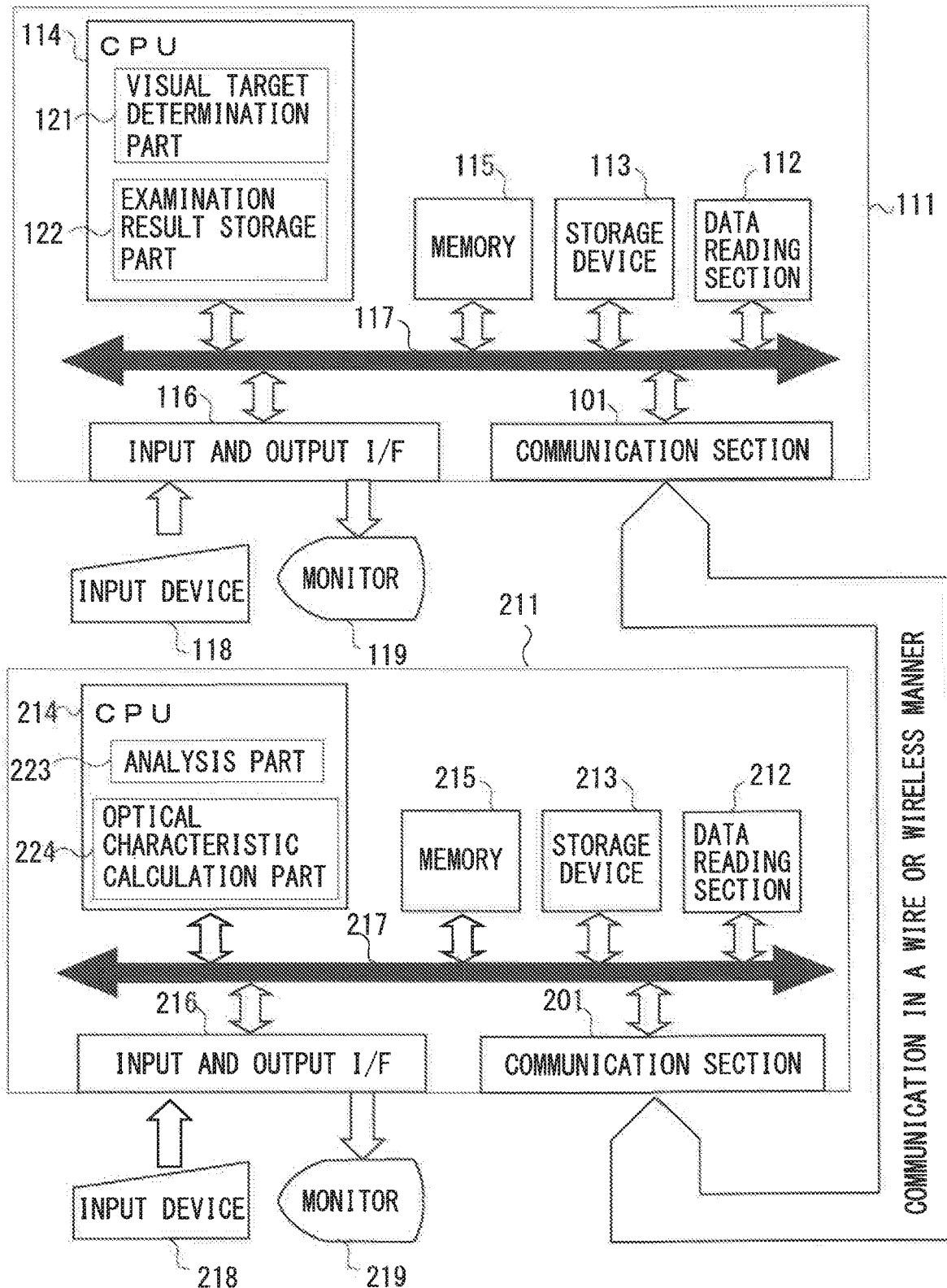
FIG. 30 is a block diagram illustrating a configuration of another visual function examination system and an optical characteristic calculation system of the embodiment.

Further, although the example in which the series of processing is completed in the visual function examination system is described in the above-described respective embodiments, it is also possible to configure such that the parts in charge of the respective pieces of processing are divided. For example, as illustrated in FIG. 30, it is also possible to configure such that the respective pieces of processing are divided between a visual function examination system having a computer 111, an input device 118, and a monitor 119, and an optical characteristic calculation system having a computer 211, an input device 218, and a monitor 219. With such a configuration, it is possible to provide the visual function examination system to a medical institution and the like in which only the visual function examination is conducted, and provide the optical characteristic calculation system to a company specialized in analysis and the like in which the analysis and the calculation of the optical characteristic are conducted.

The computer 111 in FIG. 30 includes respective parts of a data reading section 112, a storage device 113, a CPU 114, a memory 115, an input and output I/F 116, a bus 117, and a communication section 101. The configurations of the respective parts of the data reading section 112, the storage device 113, the memory 115, the input and output I/F 116, and the bus 117 are substantially the same as those of the data reading section 12, the storage device 13, the memory 15, the input and output I/F 16, and the bus 17 in FIG. 1 of the first embodiment. The respective parts of the computer 111 in FIG. 30 are comprehensively controlled by the CPU 114. The communication section 101 is a transmission/reception section for realizing communication in a wire or wireless manner between the computer 111 and an external device. The CPU 114 functions as a visual target determination part 121 and an examination result storage part 122 when a visual function examination program stored in the storage device 113 is executed. Further, the visual target determination part 121 and the examination result storage part 122 perform the visual function examination similarly to step S1 in the first embodiment or step S21 In the second embodiment. Subsequently, the result of the visual function examination is output from the communication section 101 via the bus 117 and the input and output I/F 116.

Meanwhile, the computer 211 in FIG. 30 includes respective parts of a data reading section 212, a storage device 213, a CPU 214, a memory 215, an input and output I/F 216, a bus 217, and a communication section 201. The configurations of the respective parts of the data reading section 212, the storage device 213, the memory 215, the input and output I/F 216, and the bus 217 are substantially the same as those of the data reading section 12, the storage device 13, the memory 15, the input and output I/F 16, and the bus 17 in FIG. 1 of the first embodiment. The respective parts of the computer 211 in FIG. 30 are comprehensively controlled by the CPU 214. The communication section 201 is a transmission/reception section for realizing communication in a wire or wireless manner between the computer 211 and an external device. The CPU 214 functions as an analysis part 223 and an optical characteristic calculation part 224 when an optical characteristic calculation program stored in the storage device 213 is executed. Further, the analysis part 223 and the optical characteristic calculation part 224 perform the analysis of the CA diagram and the calculation of the optical characteristic similarly to at least one of step S2 and step S3 in the first embodiment and step S22, step S23, and step S24 in the second embodiment. Note that the analysis part 223 and the optical characteristic calculation part 224 acquire the result of the visual function examination received by the communication section 201, via the input and output I/F 216 and the bus 217, and perform the analysis of the CA diagram and the calculation of the optical characteristic based on the acquired result of the visual function examination.

Note that the respective parts of the visual target determination part 121, the examination result storage part 122, the analysis part 223, and the optical characteristic calculation part 224 may also be configured in a manner of hardware by dedicated circuits.

Further, a visual function examination program and an optical characteristic calculation program are also effective as concrete examples of the present invention. These programs may be programs stored in a computer-readable medium, or programs stored in a server on the Web and capable of being downloaded to a computer via the Internet.

Further, it is also possible to consider a possibility that the technique of the above-described respective embodiments is further applied to a medical equipment or a medical device.

The many features and advantages of the embodiments are apparent from the detailed specification and, thus, it is intended by the appended claims to cover all such features and advantages of the embodiments that fall within the true spirit and scope thereof. Further, since numerous modifications and changes will readily occur to those skilled in the art, it is not desired to limit the inventive embodiments to exact construction and operation illustrated and described, and accordingly all suitable modifications and equivalents may be resorted to, falling within the scope thereof.

The invention claimed is:

1. A visual function examination system, the visual function examination system comprising:
    a display device; and
    at least one processor programmed to:
        present to a subject a plurality of visual targets displayed on the display device, each visual target including an attention portion and a background portion, and each visual target being different from each other in at least one of:
            a luminance contrast value between a luminance of the attention portion of the visual target and a luminance of the background portion of the visual target,
            a luminance average value of the visual target including the attention portion and the background portion, and
            a stimulus value of a color stimulus of the visual target,
        based on an examination result obtained from presenting the plurality of visual targets to the subject, determining, in a coordinate system indicating a correlation between the luminance contrast value and the luminance average value of each visual target, at least two boundaries between a region on the coordinate system where the subject has a visibility and a region on the coordinate system where the subject does not have the visibility for each combination of stimulus values of the color stimulus of the plurality of visual targets, and
        output an analysis result including the at least two boundaries.

2. The visual function examination system according to claim 1, wherein the at least one processor is programmed to sequentially present to the subject the plurality of visual targets.

3. The visual function examination system according to claim 1, wherein the at least one processor is programmed to:
present a first group of visual targets to the subject, the first group of visual targets having a same combination of the stimulus values of the color stimulus, and then
present a second group of visual targets to the subject, the second group of visual targets having a same combination of the stimulus values of the color stimulus that is different from the combination of the stimulus values of the color stimulus of the first group of visual targets previously presented.

4. The visual function examination system according to claim 1, wherein:
the plurality of visual targets include a glare portion at a position within a visual field of the subject; and
the glare portion is also displayed on the display device.

5. The visual function examination system according to claim 1, further comprising:
an image display configured to display, in the coordinate system, at least one boundary on the display device.

6. An optical characteristic calculation system, comprising the visual function examination system according to claim 1, wherein the at least one processor is further programmed to:
calculate an optical characteristic of an optical member for compensating a visual function of the subject based on the analysis result.

7. The optical characteristic calculation system according to claim 6, wherein
the at least one processor is programmed to calculate the optical characteristic of the optical member based on:
(a) the analysis result, and (b) a spectral distribution of a light source dominant in an environment where the subject uses the optical member.

8. The optical characteristic calculation system according to claim 6, wherein
the at least one processor is further programmed to:
acquire information indicating a light source in an environment surrounding the subject as target information of a visibility of the subject;
calculate a target value in the coordinate system based on the target information; and
calculate the optical characteristic of the optical member based on the analysis result and the target value.

9. A method comprising:
calculating an optical characteristic for compensating a visual function of the subject via the optical characteristic calculation system according to claim 6; and
selecting an optical member based on the calculated optical characteristic.

10. A method comprising:
calculating an optical characteristic for compensating a visual function of the subject via the optical characteristic calculation system according to claim 6; and
manufacturing an optical member based on the calculated optical characteristic.

11. A method of manufacturing a display member, the method comprising:
calculating an optical characteristic for compensating a visual function of the subject via the optical characteristic calculation system according to claim 6; and
manufacturing the display member based on the calculated optical characteristic.

12. A method of manufacturing an illumination apparatus, the method comprising:
calculating an optical characteristic for compensating a visual function of the subject via the optical characteristic calculation system according to claim 6; and
manufacturing the illumination apparatus based on the calculated optical characteristic.

13. The visual function examination system according to claim 1, wherein:
the region on the coordinate system where the subject has the visibility is: (i) a region indicating correlations between luminance contrast values and luminance average values of a portion of the plurality of visual targets in which the subject does not feel a glare on the attention portion, or (ii) a region indicating the correlations between the luminance contrast values and the luminance average values of the portion of the plurality of visual targets that the subject can see, and
the region on the coordinate system where the subject does not have the visibility is: (i) a region indicating correlations between luminance contrast values and luminance average values of a portion of the plurality of visual targets in which the subject feels the glare on the attention portion, or (ii) a region indicating the correlations between the luminance contrast values and the luminance average values of the portion of the plurality of visual targets that the subject cannot see.

14. A visual function examination system, the visual function examination system comprising:
an input configured to receive a result of a visual function examination obtained by sequentially presenting to a subject a plurality of visual targets, each visual target including an attention portion and a background portion, and each visual target being different from each other in at least one of:
a luminance contrast value between a luminance of the attention portion of the visual target and a luminance of the background portion of the visual target,
a luminance average value of the visual target including the attention portion and the background portion, and
a stimulus value of a color stimulus of the visual target, and
at least one processor programmed to:
based on the result of the visual function examination, determine, in a coordinate system indicating a correlation between the luminance contrast value and the luminance average value of each visual target, at least two boundaries between a region on the coordinate system where the subject has a visibility and a region on the coordinate system where the subject does not have the visibility for each combination of stimulus values of the color stimulus; and
output an analysis result including the at least two boundaries.

15. A visual function examination apparatus, the visual function examination apparatus comprising:
an image display; and
at least one processor programmed to:
present to a subject a plurality of visual targets displayed on the image display, each visual target including an attention portion and a background portion, and each visual target being different from each other in at least one of:
a luminance contrast value between a luminance of the attention portion of the visual target and a luminance of the background portion of the visual target, a luminance average value of the visual target including the attention portion and the background portion, and a stimulus value of a color stimulus of the visual target, based on an examination result obtained from presenting the plurality of visual targets to the subject, determine, in a coordinate system indicating a correlation between the luminance contrast value and the luminance average value of each visual target, at least two boundaries between a region on the coordinate system where the subject has a visibility and a region on the coordinate system where the subject does not have the visibility for each combination of stimulus values of a color stimulus of the plurality of visual targets, and output an analysis result including the at least two boundaries.

16. The visual function examination apparatus according to claim 15, wherein:

wherein the at least one processor is programmed to sequentially present the plurality of visual targets to the subject via the image display.

17. An optical characteristic calculation apparatus comprising the visual function examination apparatus according to claim 15, wherein the at least one processor is further programmed to:

calculate an optical characteristic of an optical member for compensating a visual function of the subject based on the analysis result.

18. A method for examining a visual function of a subject, comprising:

presenting a plurality of visual targets to the subject, each visual target including an attention portion and a background portion, and each visual target being different from each other in at least one of:

a luminance contrast value between a luminance of the attention portion of the visual target and a luminance of the background portion of the visual target, a luminance average value of the visual target including the attention portion and the background portion, and a stimulus value of a color stimulus of the visual target, based on an examination result obtained from presenting the plurality of visual targets to the subject, determining, in a coordinate system indicating a correlation between the luminance contrast value and the luminance average value of each visual target, at least two boundaries between a region on the coordinate system where the subject has a visibility and a region on the coordinate system where the subject does not have the visibility for each combination of stimulus values of the color stimulus of the plurality of visual targets, and outputting an analysis result including the at least two boundaries.

19. The visual function examination method according to claim 18, wherein the plurality of visual targets are sequentially presented to the subject.

20. A method of calculating an optical characteristic, the method comprising:

performing the method according to claim 18 to obtain the analysis result; and calculating an optical characteristic of an optical member for compensating a visual function of the subject based on the analysis result.

21. A non-transitory computer-readable storage medium storing a program, the program causing a computer to execute:

displaying a plurality of visual targets on an image display, each visual target including an attention portion and a background portion, and each visual target being different from each other in at least one of:

a luminance contrast value between a luminance of the attention portion of the visual target and a luminance of the background portion of the visual target, a luminance average value of the visual target including the attention portion and the background portion, and a stimulus value of a color stimulus of the visual target, based on an examination result obtained from presenting the plurality of visual targets displayed on the image display to a subject, determining, in a coordinate system indicating a correlation between the luminance contrast value and the luminance average value of each visual target, at least two boundaries between a region on the coordinate system where a subject has a visibility and a region on the coordinate system where the subject does not have the visibility for each combination of stimulus values of the color stimulus of the plurality of visual targets, and outputting an analysis result including the at least two boundaries.

22. The non-transitory computer-readable storage medium according to claim 21, wherein the plurality of visual targets are sequentially displayed on the image display.

23. The non-transitory computer-readable storage medium according to claim 21, wherein the program further causes the computer to execute:

calculating an optical characteristic of an optical member based on at least one of:

the examination result, and the analysis result.

* * * * *